(12) United States Patent
Fukuda et al.

(10) Patent No.: US 11,059,881 B2
(45) Date of Patent: Jul. 13, 2021

(54) METHOD FOR MEASURING VISCOSITY OF PROTEIN SOLUTION

(71) Applicant: CHUGAI SEIYAKU KABUSHIKI KAISHA, Tokyo (JP)

(72) Inventors: Masakazu Fukuda, Tokyo (JP); Akira Hayasaka, Shizuoka (JP); Tomoyuki Igawa, Shizuoka (JP); Atsuhiko Maeda, Shizuoka (JP); Machiko Fujino, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/742,053

(22) Filed: Jan. 14, 2020

(65) Prior Publication Data

US 2020/0131250 A1 Apr. 30, 2020

Related U.S. Application Data

(63) Continuation of application No. 15/503,441, filed as application No. PCT/JP2015/073392 on Aug. 20, 2015, now abandoned.

(30) Foreign Application Priority Data

Aug. 20, 2014 (JP) ................................ 2014-167907
Dec. 12, 2014 (JP) ................................ 2014-252187
Apr. 1, 2015 (JP) ................................ 2015-075485

(51) Int. Cl.
| | | |
|---|---|---|
| *G01N 33/68* | (2006.01) | |
| *G01N 11/00* | (2006.01) | |
| *G01N 23/201* | (2018.01) | |
| *C07K 16/00* | (2006.01) | |
| *C07K 16/18* | (2006.01) | |
| *C07K 16/28* | (2006.01) | |
| *C07K 16/30* | (2006.01) | |
| *C07K 16/36* | (2006.01) | |

(52) U.S. Cl.
CPC ............. *C07K 16/00* (2013.01); *C07K 16/18* (2013.01); *C07K 16/2866* (2013.01); *C07K 16/303* (2013.01); *C07K 16/36* (2013.01); *G01N 11/00* (2013.01); *G01N 23/201* (2013.01); *G01N 33/6803* (2013.01); *G01N 33/6854* (2013.01); *C07K 2317/24* (2013.01); *C07K 2317/31* (2013.01); *C07K 2317/90* (2013.01); *C07K 2317/94* (2013.01)

(58) Field of Classification Search
CPC .... C07K 16/00; C07K 16/18; C07K 16/2866; C07K 16/303; C07K 16/36; C07K 2317/24; C07K 2317/31; C07K 2317/90; C07K 2317/94; G01N 11/00; G01N 23/201; G01N 33/68; G01N 33/6803; G01N 33/6854

USPC ............................................ 436/86, 89, 513
See application file for complete search history.

(56) References Cited

U.S. PATENT DOCUMENTS

| 4,816,397 A | 3/1989 | Boss et al. |
| 4,816,567 A | 3/1989 | Cabilly et al. |

FOREIGN PATENT DOCUMENTS

| EP | 0 173 494 | 3/1986 |
| EP | 0 173 494 | 3/1989 |
| EP | 0 402 012 | 12/1990 |
| EP | 2 762 564 | 8/2014 |
| GB | 1551074 | 8/1979 |
| JP | 52-52908 | 4/1977 |
| JP | H02-309230 | 12/1990 |
| JP | 2009/500344 | 1/2009 |
| WO | WO 2007/005612 | 1/2007 |
| WO | WO 2013/046722 | 4/2013 |
| WO | WO 2013/100120 | 7/2013 |

OTHER PUBLICATIONS

Connolly et al., "Weak Interactions Govern the Viscosity of Concentrated Antibody Solutions: High-Throughput Analysis Using the Diffusion Interaction Parameter," Biophys J, Jul. 3, 2012, 103(1):69-78. doi: 10.1016/j. bpj. 2012. 04. 047.
International Search Report in International Application No. PCT/JP2015/073392, dated Nov. 24, 2015, 2 pages.
Fukuda et al., "Quantitative Correlation between Viscosity of Concentrated MAb Solutions and Particle Size Parameters Obtained from Small-Angle X-ray Scattering," Pharm Res, Dec. 2015, 32(12):3803-12. doi: 10.1007/s11095-015-1739-6 Epub Jun. 16, 2015.
Saito et al., "Behavior of Monoclonal Antibodies: Relation Between the Second Virial Coefficient ($B_2$) at Low Concentrations and Aggregation Propensity and Viscosity at High Concentrations," Pharm Res, Feb. 2012, 29(2):397-410. doi: 10. 1007/s11095-011-0563-x. Epub Aug. 19, 2011.
Sarangapani et al., "The Limitations of an Exclusively Colloidal View of Protein Solution Hydrodynamics and Rheology," Biophys J, Nov. 19, 2013, 105(10):2418-26. doi: 10.1016/j.bpj.2013.10.012.
Sato, "A Dissipative Structure of $F_1$•ATP Synthase $\alpha_3\beta_3$ Complex," Journal of the Japanese Society for Synchrotron Radiation Research, 1993, 6(1):25-36 (with partial English translation).
Singh et al., "Dipole-Dipole Interaction in Antibody Solutions: Correlation with Viscosity Behavior at High Concentration," Pharm Res, Sep. 31, 2014(9): 2549-58. doi: 10. 1007/s11095-014-1352-0. Epub Mar. 18, 2014.

(Continued)

*Primary Examiner* — Maureen Wallenhorst
(74) *Attorney, Agent, or Firm* — Fish & Richardson P.C.

(57) ABSTRACT

The inventors discovered that viscosity of a protein solution can be estimated by measuring the apparent particle size or apparent molecular weight by a small angle X-ray scattering (SAXS) method or X-ray solution scattering method, which enables measurement of small amounts of samples, and then correlating those measurement results with viscosity of the protein solution.

84 Claims, 6 Drawing Sheets

Specification includes a Sequence Listing.

(56) References Cited

OTHER PUBLICATIONS

Yadav et al., "The Influence of Charge Distribution on Self-Association and Viscosity Behavior of Monoclonal Antibody Solutions," Mol Pharm, Apr. 2, 2012, 9(4):791-802. doi: 10.1021/mp200566k. Epub Mar. 19, 2012.
Yadav et al., "Viscosity Behavior of High-Concentration Monoclonal Antibody Solutions: Correlation with Interaction Parameter and Electroviscous Effects," J Pharm Sci, Mar. 2012, 101(3):998-1011. doi: 10.1002/jps. 22831. Epub Nov. 23, 2011.
Yearley et al., "Observation of Small Cluster Formation in Concentrated Monoclonal Antibody Solutions and Its Implications to Solution Viscosity," Biophys J, Apr. 15, 2014, 106(8):1763-70. doi: 10.1016/j.bpj. 2014. 02.036.
Yearley et al., "Small-Angle Neutron Scattering Characterization of Monoclonal Antibody Conformations and Interactions at High Concentrations," Biophys J, Aug. 6, 2013, 105(3):720-31. doi: 10.1016/j.bpj. 2013. 06. 043.
Yuzawa, "Solution structure of signaling protein Grb2 composed of three domains by Small Angle X-ray Scattering," Photon Fact News, 2002, (19)4:20-24 (with English translation).
USPTO Restriction Requirement in U.S. Appl. No. 15/503,441, dated Dec. 18, 2018, 8 pages.
USPTO Non-Final Office Action in U.S. Appl. No. 15/503,441, dated Jul. 15, 2019, 16 pages.
He et al., "High-throughput dynamic light scattering method for measuring viscosity of concentrated protein solutions," Anal Biochem, Apr. 1, 2010, 399(1):141-143. doi: 10.1016/j.ab.2009.12.003. Epub Dec. 6, 2009.

SEQUENCE LISTING

```
<160> NUMBER OF SEQ ID NOS: 5

<210> SEQ ID NO 1
<211> LENGTH: 443
<212> TYPE: PRT
<213> ORGANISM: Artificial Sequence
<220> FEATURE:
<223> OTHER INFORMATION: An artificially synthesized peptide sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 2
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45
```

```
Tyr Tyr Gly Ser His Leu Leu Ser Gly Val Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                 85                  90                  95

Thr Phe Gly Gln Gly Thr Lys Val Glu Ile Glu Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 3
<211> LENGTH: 448
<212> TYPE: PRT
<213> ORGANISM: Artificial
<220> FEATURE:
<223> OTHER INFORMATION: An artificially synthesized peptide sequence

<400> SEQUENCE: 3

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
                20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Gly Arg Glu Tyr Gly Gly Trp Tyr Phe Asp Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
                420                 425                 430

Glu Ala Leu His Asn Arg Tyr Thr Gln Lys Ser Leu Ser Leu Ser Pro
        435                 440                 445

<210> SEQ ID NO 4
<211> LENGTH: 444
<212> TYPE: PRT
<213> ORGANISM: Artificial
<220> FEATURE:
<223> OTHER INFORMATION: An artificially synthesized peptide sequence

<400> SEQUENCE: 4

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
        50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
            435                 440

<210> SEQ ID NO 5
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

-continued

```
Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210
```

METHOD FOR MEASURING VISCOSITY OF PROTEIN SOLUTION

CROSS-REFERENCE TO RELATED APPLICATIONS

This application is a continuation of U.S. application Ser. No. 15/503,441, filed on Feb. 13, 2017, which is the National Stage of International Application No. PCT/JP2015/073392, filed on Aug. 20, 2015, which claims the benefit of Japanese Application Nos. 2014-167907, 2014-252187, and 2015-075485, filed on Aug. 20, 2014, Dec. 12, 2014, and Apr. 1, 2015, respectively.

TECHNICAL FIELD

The present invention relates to methods for measuring viscosity of a protein solution, and particularly to methods for measuring viscosity of a protein solution with a small quantity of sample.

BACKGROUND ART

Recently, pharmaceutical preparations containing proteins such as antibodies as an active ingredient are being developed into solution preparations for use in subcutaneous administration, in consideration of their convenience and such. Along with this, the protein such as an antibody as an active ingredient in the drug solutions is being used at higher concentrations. When developing a high-concentration protein drug solution, the viscosity of the solution greatly affects manufacturability and usability of the solution. Therefore, viscosity is a physical property issue that greatly affects the overall development. The increase of solution viscosity (high viscosity) accompanying the increase of concentration is considered to be caused by electrostatic attraction due to uneven distribution of charges on the surface of the protein molecules and the resulting molecular association (cluster formation) (Non-patent Document 1). That is, since high viscosity is caused by the properties of the protein molecule itself, it is difficult to reduce viscosity with absolute certainty through formulation design. In addition, when the intention is to develop highly manufacturable and usable protein preparations with low viscosity, one must select molecules with low viscosity at the time of developing those molecules.

However, large quantities of samples are required to obtain actual values for viscosity at high concentrations, and thus it is impractical to perform viscosity evaluation in the early stages of development when candidate molecules are being assessed. Therefore, it is desired to establish an evaluation system in which the viscosity at a high concentration can be predicted by using a small amount of sample.

So far, parameters showing the strength of interaction between antibody molecules, which can be obtained from dynamic light scattering measurements of low-concentration samples, have been reported to correlate with the viscosity at a high concentration. However, only rough correlations have been observed; and particularly with regard to antibodies with strongly working intermolecular interactions, there were problems with the precision of the parameters when considering them as a viscosity prediction system (Non-patent Documents 2 to 4).

Small angle X-ray scattering (SAXS) is a technique of obtaining information relating to the shape of particles in a sample with a small amount (10 µL) of the sample, by irradiating the sample with X rays and analyzing the dependence of scattering intensity on scattering angle (scattering profile). However, using this technique to obtain parameters for measuring the viscosity of a protein solution has not been known.

PRIOR ART DOCUMENTS

Non-Patent Documents

[Non-patent Document 1] Pharm Res. 31:2549-2558 (2014)
[Non-patent Document 2] Pharm Res. 29:397-410 (2012)
[Non-patent Document 3] J Pharm Sci. 101:998-1011 (2012)
[Non-patent Document 4] Biophys J. 103:69-78 (2012)

SUMMARY OF THE INVENTION

Problems to be Solved by the Invention

An objective of the present invention is to provide a method for measuring the viscosity of a protein solution, a method for predicting the viscosity of a protein, a method for selecting a protein with regulated viscosity, a method for producing a modified protein with regulated viscosity, a method for producing a modified protein with decreased viscosity, and a method for producing a protein with low viscosity, which can be carried out particularly with a small amount of sample.

Generally, for measuring the viscosity of protein solutions such as antibody solutions, a rheometer which calculates viscosity from a proportionality coefficient of shearing velocity and shearing stress, an EMS viscometer which calculates viscosity from the speed of rotation of a metal ball in a sample solution, or a viscosity measuring device using a microchannel that calculates viscosity from the passing speed or pressure loss during passage of a sample is mainly used.

However, viscosity measurement using a rheometer or an EMS viscometer requires large amounts of samples, and sample preparation work is also complicated. Therefore, it was difficult to measure many samples at the same time. Furthermore, in viscosity measurements using a microchannel, it was difficult to measure viscosity of highly adsorptive protein solutions with high accuracy and reproducibility. Therefore, it was not possible to use viscosity as an indicator to screen for modified proteins by taking various types of measurements with a small amount of sample.

Means for Solving the Problems

As a result of dedicated research to achieve the above-mentioned objectives, the present inventors discovered that by utilizing the small angle X-ray scattering (SAXS) technique which has been conventionally used in analyses of molecular shapes of proteins in solutions and such, the viscosity of a protein solution can be measured (estimated) with accuracy by using a trace amount of a solution sample containing the protein.

Conventionally, in molecular shape analysis using SAXS, in the case of a protein whose three-dimensional structure is complex, the shape is usually evaluated under low-concentration conditions where intermolecular interactions can be neglected. However, in the present invention, apparent shape information, i.e. apparent particle size, was determined by deliberately using an analytical method that assumes absence of the interactions in a relatively high-concentration range where the interactions, i.e. molecular association, are observed. The inventors predicted that the estimate of this parameter would be a large value due to occurrence of association from strong intermolecular interactions, and hypothesized that this parameter correlates with the viscosity of a protein solution when made at a high concentration.

To prove this hypothesis, actual viscosity values were obtained at room temperature (25° C.) for varying types of antibodies and solvents at a high concentration (200 mg/mL). Meanwhile, apparent particle size at semi-low concentration (60 mg/mL) was evaluated under the same conditions by SAXS measurement, and the two were found to have a very good correlation. Furthermore, with an expectation that differences in associativity among the samples can be evaluated at a lower concentration by performing SAXS measurements at low temperature, the inventors evaluated apparent particle size and apparent molecular weight at 5° C./15 mg/mL, and found that the results correlate well with the viscosity determined at 25° C./160 mg/mL. That is, the viscosity of a high-concentration antibody preparation at room temperature was shown to be predictable from the apparent particle size and apparent molecular weight obtainable from SAXS measurements at low temperature by using a small amount (15 mg/mL, 10 μL) of the sample.

More specifically, the present invention provides the following:

[1] A method for measuring viscosity of a protein solution, which comprises the steps of:
  1) irradiating a sample with an X-ray, wherein the protein concentration in the sample is 1 mg/mL to 100 mg/mL to determine apparent particle size (apparent maximum particle diameter ($D_{max}^{app}$) or apparent particle radius of gyration ($R_g^{app}$)), or apparent molecular weight by a small angle X-ray scattering (SAXS) method or X-ray solution scattering method; and
  2) calculating viscosity of the protein from the above-determined value based on a calibration curve obtained in advance;
[2] the measurement method of [1], wherein the protein concentration in the sample is 10 to 100 mg/mL;
[3] the measurement method of [1] or [2], wherein the protein concentration in the sample is 10 to 30 mg/mL;
[4] the measurement method of any one of [1] to [3], wherein the protein concentration in the sample is 15 to 30 mg/mL;
[5] the measurement method of any one of [1] to [4], wherein a temperature condition for the measurement is 0° C. to 40° C.;
[6] the measurement method of any one of [1] to [5], wherein a temperature condition for the measurement is 0° C. to 25° C.;
[7] the measurement method of any one of [1] to [6], wherein a temperature condition for the measurement is 3° C. to 10° C.;
[8] the measurement method of any one of [1] to [7], wherein the amount of the sample to be measured is 1 μL to 100 μL;
[9] the measurement method for measuring of any one of [1] to [8], wherein the amount of the sample to be measured is 54 to 30 μL;
[10] the measurement method of any one of [1] to [9], wherein the protein is an antibody;
[11] a method for predicting viscosity of a protein, which comprises irradiating a sample with an X-ray, wherein the protein concentration in the sample is 1 mg/mL to 100 mg/mL, to determine apparent particle size (apparent maximum particle diameter ($D_{max}^{app}$) or apparent particle radius of gyration ($R_g^{app}$)) or apparent molecular weight by a small angle X-ray scattering (SAXS) method or X-ray solution scattering method;
[12] a method for selecting a viscosity-regulated protein, which comprises irradiating a sample with an X-ray, wherein the protein concentration in the sample is 1 mg/mL to 100 mg/mL, to determine apparent particle size (apparent maximum particle diameter ($D_{max}^{app}$) or apparent particle radius of gyration ($R_g^{app}$)) or apparent molecular weight by a small angle X-ray scattering (SAXS) method or X-ray solution scattering method;
[13] a method for producing a modified protein with regulated viscosity, which comprises the steps of:
  1) obtaining a modified protein by modifying a portion of the amino acids of an original protein; and
  2) predicting viscosity of the protein by using the prediction method of [11];
[14] a method for producing a protein with low viscosity, which comprises the step of:
  1) selecting a protein with low viscosity by using the prediction method of [11];
[15] a method for producing a modified protein with regulated viscosity, which comprises the steps of:
  1) obtaining a modified protein by modifying a portion of the amino acids of an original protein; and
  2) selecting a protein with regulated viscosity from the modified protein by using the selection method of [12];
[16] a method for producing a modified protein with decreased viscosity, which comprises the steps of:
  1) obtaining a modified protein by modifying a portion of the amino acids of an original protein; and
  2) selecting from the modified protein, a modified protein with viscosity lower than that of the original protein by using the selection method of [12];
[17] the method of any one of [13], [15], and [16], wherein the original protein is a modified protein in which a portion of the amino acid residues is substituted with histidine (His) residues;
[18] the method of any one of [11] to [16], wherein the protein is an antibody;
[19] a modified antibody produced by substituting a portion of the amino acid residues of an original antibody with histidine (His) residues, whose amino acid residue at position 97 according to the Kabat numbering system is not a His residue;
[20] the modified antibody of [19], wherein the amino acid residue at position 97 is the amino acid residue of the original antibody;
[21] a modified antibody showing ion concentration-dependent antigen binding, which is produced by substituting a portion of the amino acid residues of an original antibody with other amino acids, wherein the amino acid residue at position 97 according to the Kabat numbering system is not a His residue; and
[22] the modified antibody of [21], wherein the amino acid residue at position 97 is the amino acid residue of the original antibody.

MODE FOR CARRYING OUT THE INVENTION

Figure 1:
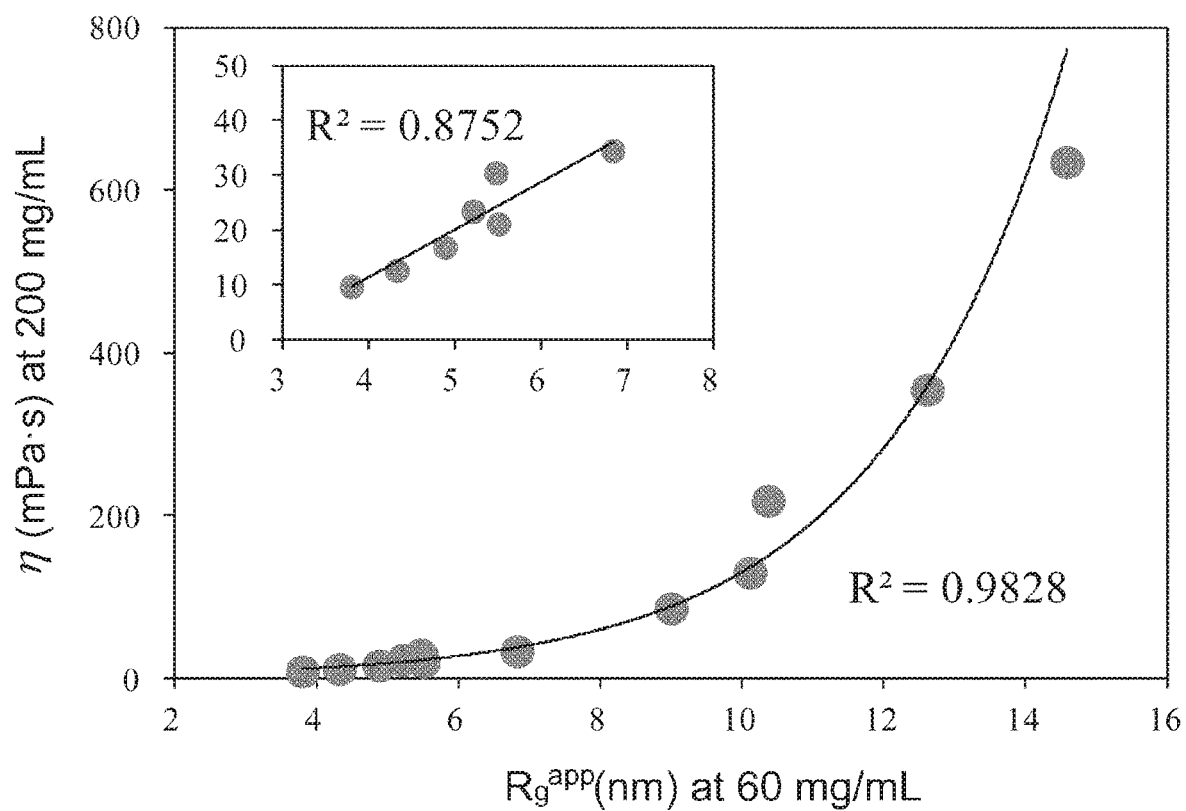
FIG. 1 is a graph showing the result of plotting the viscosity of each antibody solution obtained as a function of $R_g^{app}$ at 60 mg/mL and at 15° C. to 35° C. from SAXS measurements.

The present invention will be described in detail below.

The present invention relates to a method for measuring (method for estimating) the viscosity of a protein solution, a method for predicting the viscosity of a protein, a method for selecting a viscosity-regulated protein, a method for producing a modified protein with regulated viscosity, a method for producing a modified protein with decreased viscosity, and a method for producing a protein with low viscosity, which can be carried out by using a small amount of sample.

In the method of the present invention, even a small amount of a protein solution at a relatively low concentration can be used to accurately estimate its viscosity at a high concentration.

Specifically, by (1) irradiating a sample with 1 mg/mL to 100 mg/mL protein concentration with an X-ray, and using the small angle X-ray scattering (SAXS) method or the X-ray solution scattering method to determine apparent particle size (apparent maximum particle diameter ($D_{max}^{app}$) or apparent particle radius of gyration ($R_g^{app}$)) or apparent molecular weight; and (2) calculating the viscosity of the protein from the above-determined value based on a calibration curve obtained in advance, one can estimate the viscosity of the protein-containing solution at a high concentration.

Furthermore, by using the above-mentioned measurement values, it is possible to predict protein viscosity and select viscosity-regulated proteins. In the present invention, a "viscosity-regulated protein" or a "protein with regulated viscosity" means a protein having viscosity within the desired viscosity range when existing in solution, or preferably a protein whose viscosity, which is increased when the protein is concentrated to a higher level, is regulated to the desired viscosity range, and examples include proteins having a viscosity within a suitable range for use as active ingredients in protein solution preparations as pharmaceuticals (preferably solution preparations for subcutaneous administration). While the viscosity range can be appropriately set by those skilled in the art, it is preferably a viscosity range where the manufacturability and usability of a protein solution preparation are high, for example, 2000 mPa·s or less, preferably 1500 mPa·s or less, more preferably 0.1 mPa·s to 1000 mPa·s, and particularly preferably 1 mPa·s to 700 mPa·s at normal temperature to body temperature (15° C. to 40° C.).

Furthermore, predicting the viscosity of modified proteins obtained by various methods using the above-mentioned prediction methods enables efficient production of the modified proteins with regulated viscosity (or reduced viscosity). Various modification methods are known as methods for modifying some amino acids in the original protein to obtain modified proteins, and those skilled in the art can appropriately make a selection from these known methods, partially alter the method in certain cases, and carry out the modification. In one embodiment, the original protein in the method for producing modified proteins of the present invention is a modified protein in which some of the amino acid residues have been substituted with histidine (His) residues. The present invention also relates to modified proteins produced by such production methods. The protein is preferably a mutant antibody, and more preferably a mutant antibody produced by substituting some of the amino acid residues of the original antibody with histidine (His) residues, wherein the amino acid residue at position 97 according to the Kabat-numbering system is not a His residue, and wherein the amino acid residue at position 97 is the amino acid residue of the original antibody. More preferably, it is an antibody with a viscosity lower than that of the antibody whose amino acid residue at position 97 has been substituted with His.

Here, the term "original protein" or "original antibody" refers to the "protein before being artificially modified at some of its amino acids" or the "antibody before being artificially modified at some of its amino acids".

Furthermore, by using the above-mentioned prediction method to select proteins with a low viscosity, low-viscosity proteins or modified proteins with a reduced viscosity can be produced efficiently. In the present invention, "low-viscosity protein" or "modified protein with a reduced viscosity" or "modified reduced-viscosity protein" refers to a protein having a viscosity within the above-mentioned viscosity range.

The amount of a sample to be used in the method of the present invention is not particularly limited as long as it is an amount that allows measurement of the apparent particle size or apparent molecular weight, and examples include 34 to 100 μL, preferably 3 μL to 50 μL, and particularly preferably 5 μL to 30 μL. The protein concentration in the sample to be used for the method of the present invention is not particularly limited as long as it is a concentration that allows measurement of the apparent particle size or apparent molecular weight; and examples are preferably 1 mg/mL to 100 mg/mL, more preferably 10 mg/mL to 100 mg/mL, and even more preferably 15 mg/mL to 30 mg/mL. Protein solutions of a lower concentration can be a subject for measurement by performing SAXS measurements at a low temperature (for example 3° C. to 10° C.). As such, since viscosity measurement and viscosity prediction are possible with low-concentration samples at small amounts, the method of the present invention can be used to efficiently select (screen) viscosity-regulated proteins, proteins with reduced viscosity, or modified low-viscosity proteins, and to efficiently produce such modified proteins.

Methods of the present invention use a good correlation between protein solution viscosity and the above-mentioned particle size parameters (apparent maximum particle diameter ($D_{max}^{app}$) or apparent particle radius of gyration ($R_g^{app}$)), or apparent molecular weight to predict the viscosity of the protein solution from measured values of the apparent particle size or apparent molecular weight. This correlation is a positive correlation where an increase in protein solution viscosity correlates with an increase in the measured value of apparent particle size or apparent molecular weight, and this is preferably an exponential correlation or linear correlation. The temperature condition for measuring the aforementioned particle size parameter is not limited as long as it is in a temperature range that allows the measurement, and examples include 40° C. or lower, preferably room temperature or lower, more preferably 0° C. to 25° C., and particularly preferably 3° C. to 10° C.

In one embodiment, the method for measuring (estimating) the viscosity of a protein solution of the present invention comprises the steps of:

(1) irradiating a sample with 1 mg/mL to 100 mg/mL protein concentration with an X-ray, and using the small angle X-ray scattering (SAXS) method or the X-ray solution scattering method to determine the apparent particle size (apparent maximum particle diameter ($D_{max}^{app}$) or apparent particle radius of gyration ($R_g^{app}$)) or apparent molecular weight of the protein in the solution; and (2) calculating the viscosity of the protein from the above-determined value based on a calibration curve obtained in advance.

In the present invention, the apparent maximum particle diameter ($D_{max}^{app}$) or apparent particle radius of gyration ($R_g^{app}$), which are particle size parameters for protein solutions, can be calculated as described in the Examples of this application. Furthermore, the apparent molecular weight is given as a value proportional to the scattering intensity ($I(0)$) at a scattering angle of zero. Scattering patterns of samples subjected to X-ray irradiation, which are used to calculate these parameters, can be detected by methods known to those skilled in the art by the small angle X-ray scattering (SAXS) method or the X-ray solution scattering method.

In certain embodiments, the calibration curve used in step (2) above can be determined by analyzing the correlation between viscosity and the apparent particle size or apparent molecular weight measured for various pairs of protein solutions and SAXS measurement samples. In this analysis, the type of protein and the solvent should be the same within the pair of protein solutions subjected to viscosity measurement and a sample subjected to SAXS measurement, while the protein concentration and the measurement temperature do not have to be the same for these measurements. Therefore, viscosity which is the subject of the correlation analysis is not limited to the viscosity measured under conditions identical to those in step (1) above, and thus by preparing a calibration curve for the viscosity measured under desired conditions and using it in step (2) above, the viscosity under such conditions (for example, room-temperature viscosity at a high concentration) can be estimated. Since the calibration curve can be applied to solutions of different proteins, the protein in the solution subjected to the correlation analysis in this step may be the same as or different from the protein in the solution used in steps (1) to (2) above, and the correlation analysis can be carried out using the measurement results for protein solutions composed of various proteins and solvents.

The proteins used in the present invention are not particularly limited as long as they are proteins whose apparent particle size or apparent molecular weight can be measured by the small angle X-ray scattering (SAXS) method or the X-ray solution scattering method, and are preferably proteins expected to be developed into high-concentration protein solution formulations, and examples include albumins such as BSA and antibodies.

Antibodies used in the present invention are not particularly limited as long as they bind to the desired antigens; and while they may be polyclonal antibodies or monoclonal antibodies, monoclonal antibodies are preferred since they enable stable production of homogeneous antibodies.

The monoclonal antibodies used in the present invention include not only those derived from animals such as humans, mice, rats, hamsters, rabbits, sheep, camels, and monkeys, but also artificially engineered recombinant antibodies such as chimeric antibodies, humanized antibodies, and bispecific antibodies. These antibodies also include recombinant antibodies that result from artificially engineering the antibody constant regions and such to alter the physical properties of the antibody molecule (specifically, alteration of the isoelectric point (pI), alteration of the Fc receptor affinity, etc.) for the purpose of increasing blood retention or in vivo kinetics.

The immunoglobulin class of the antibodies used in the present invention is not particularly limited, and the class may be any class, including IgG such as IgG1, IgG2, IgG3, and IgG4, IgA, IgD, IgE, and IgM. However, IgG and IgM are preferred.

The antibodies used in the present invention also include not only antibodies that have constant regions and variable regions (whole antibodies) but also antibody fragments such as Fv, Fab, and F(ab)$_2$, and low-molecular-weight antibodies (minibodies) such as mono-, bi-, or multi-valent single-chain Fv (scFv, sc(Fv)$_2$) that result from linking antibody variable regions via a linker such as peptide linker, and diabodies such as scFv dimer; however, whole antibodies are preferred.

The above-described antibodies used in the present invention can be prepared by methods known to those skilled in the art. Basically, monoclonal antibody-producing hybridomas can be prepared by using known techniques such as those described below. More specifically, immunization is carried out by a conventional immunization method using a desired antigen or cells expressing the desired antigen as a sensitizing antigen. The resulting immune cells are fused with known parental cells by a conventional cell fusion method. The fused cells are screened for monoclonal antibody-producing cells (hybridomas) by conventional screening methods to produce the antibodies. Hybridomas can be generated, for example, according to the method of Milstein et al. (Kohler, G. and Milstein, C., Methods Enzymol. (1981) 73: 3-46). When an antigen has low immunogenicity, immunization can be performed by linking the antigen to an immunogenic macromolecule such as albumin.

Alternatively, it is possible to use recombinant antibodies produced using gene recombination techniques in which antibody genes are cloned from hybridomas and inserted into appropriate vectors, and the resulting vectors are introduced into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs for antibody variable regions (V regions) are synthesized from mRNAs of the hybridomas using reverse transcriptase. When a DNA encoding an antibody V region of interest is obtained, the DNA is linked to a DNA encoding a desired antibody constant region (C region). The resulting construct is inserted into an expression vector. Alternatively, the antibody V region-encoding DNA may be inserted into an expression vector carrying the DNA of the antibody C region. The resulting construct is inserted into an expression vector so that it is expressed under the control of an expression regulatory region, for example, an enhancer or a promoter. Then, host cells are transformed with the expression vector to express the antibody.

In the present invention, artificially modified recombinant antibodies, for example, chimeric and humanized antibodies can be used to reduce heterologous antigenicity against humans, and such. Such modified antibodies can be produced using known methods. A chimeric antibody is an antibody consisting of the heavy-chain and light-chain variable regions of an antibody from a non-human mammal such as mouse, and the heavy-chain and light-chain constant regions of a human antibody. The chimeric antibody can be obtained by linking a DNA encoding the variable regions of a mouse antibody to a DNA encoding the constant regions of a human antibody, inserting it into an expression vector, and then introducing the vector into a host to produce the antibody.

A humanized antibody is also referred to as a reshaped human antibody, and is obtained by transplanting the complementarity determining region (CDR) of an antibody derived from a non-human mammal such as mouse into the complementarity determining region of a human antibody. Its general gene recombination techniques are known. Specifically, a DNA sequence is designed to have a mouse antibody CDR linked to a human antibody framework region (FR), and is synthesized by PCR using several oligonucleotides prepared to have overlapping portions at their ends. The obtained DNA is ligated to a DNA encoding a human antibody constant region and then inserted into an expression vector. The expression vector is introduced into a host to produce the humanized antibody (see European Patent Application Publication No. EP 239400 and WO 96/02576). The CDR-linked human antibody FR is selected so that the complementarity determining region forms a preferable antigen-binding site. Amino acids in the framework region of the antibody variable region can be substituted as required so that the complementarity determining region of the reshaped human antibody forms a suitable antigen-binding site (Sato, K. et al., Cancer Res. (1993) 53, 851-856). Techniques for substituting amino acid(s) in an antibody to increase activities, physical properties, pharmacokinetics, safety, and such of the antibody are known, and examples of such techniques are described below. The antibodies used in the present invention also include those having such amino acid substitutions (and including also deletions and additions).

Techniques have been reported for substituting amino acid(s) in the IgG antibody variable regions, and include humanization (Tsurushita N, Hinton P R, Kumar S., Design of humanized antibodies: from anti-Tac to Zenapax., Methods. 2005 May; 36(1): 69-83); affinity maturation to enhance the binding activity via amino acid substitution in the complementarity determining region (CDR) (Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc Natl Acad Sci USA. 2005 Jun. 14; 102(24): 8466-71); and improvement of physicochemical stability via amino acid substitution in the framework (FR) (Ewert S, Honegger A, Pluckthun A., Stability improvement of antibodies for extracellular and intracellular applications: CDR grafting to stable frameworks and structure-based framework engineering., Methods. 2004 October; 34(2): 184-99. Review). There are also known techniques for enhancing antibody-dependent cellular cytotoxicity (ADCC) and complement-dependent cytotoxicity (CDC) by substituting amino acid(s) in the IgG antibody Fc region (Kim S J, Park Y, Hong H J., Antibody engineering for the development of therapeutic antibodies., Mol Cells. 2005 Aug. 31; 20(1): 17-29. Review). Furthermore, in addition to such techniques for enhancing effector functions, there are reports on techniques for increasing the antibody half-life in blood by substituting amino acid(s) in Fc (Hinton P R, Xiong J M, Johlfs M G, Tang M T, Keller S, Tsurushita N., An engineered human IgG1 antibody with longer serum half-life., J Immunol. 2006 Jan. 1; 176(1): 346-56; Ghetie V, Popov S, Borvak J, Radu C, Matesoi D, Medesan C, Ober R J, Ward E S., Increasing the serum persistence of an IgG fragment by random mutagenesis., Nat. Biotechnol. 1997 July; 15(7): 637-40). Various techniques of substituting amino acid(s) in the constant regions for the purpose of increasing the physical properties of an antibody are also known (WO 09/41613).

Methods for obtaining human antibodies are also known. For example, desired human antibodies with antigen-binding activity can be obtained by sensitizing human lymphocytes in vitro with an antigen of interest or with cells expressing an antigen of interest; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by immunizing transgenic animals having the entire repertoire of human antibody genes with an antigen (see WO 93/12227, WO 92/03918, WO 94/02602, WO 94/25585, WO 96/34096, and WO 96/33735). Furthermore, techniques for obtaining human antibodies by panning with a human antibody library are known. For example, the variable regions of human antibodies are expressed as single-chain antibodies (scFvs) on the surface of phages using a phage display method, and then phages that bind to the antigen can be selected. Genes of the selected phages can be analyzed to determine DNA sequences that encode the variable regions of the human antibodies that bind to the antigen. When the DNA sequences of scFvs that bind to the antigen are identified, appropriate expression vectors carrying these sequences can be constructed to obtain human antibodies. Such methods are already well known, and WO 92/01047, WO 92/20791, WO 93/06213, WO 93/11236, WO 93/19172, WO 95/01438, and WO 95/15388 can be used as reference. The antibodies used in the present invention also include such human antibodies.

When an antibody gene is isolated and then introduced into appropriate hosts to produce antibodies, hosts and expression vectors can be used in appropriate combinations. When eukaryotic cells are used as the host, animal cells, plant cells, and fungal cells can be used. Known animal cells include: (1) mammalian cells, for example, CHO, COS, myeloma, baby hamster kidney (BHK), HeLa, and Vero; (2) amphibian cells, for example, *Xenopus* oocytes; and (3) insect cells, for example, sf9, sf21, and Tn5. Known plant cells include cells derived from the genus *Nicotiana* such as *Nicotiana tabacum*, which can be cultured as a callus. Known fungal cells include yeasts such as the genus *Saccharomyces*, for example, *Saccharomyces cerevisiae*, and filamentous fungi such as the genus *Aspergillus*, for example, *Aspergillus niger*. When using prokaryotic cells, production systems using bacterial cells can be used. Known bacterial cells include *Escherichia coli* (*E. coli*) and *Bacillus subtilis*. Antibodies can be obtained by introducing the antibody genes of interest into these cells by transformation and then culturing the transformed cells in vitro.

The antibodies used in the present invention also include antibody fragments, minibodies, and antibody modification products. Antibody fragments and minibodies include, for example, Fab, F(ab')2, Fv, or mono-, bi-, or multi-valent single-chain Fv (scFv, sc(Fv)$_2$, or such) that result from linking the H chain and L chain Fvs via appropriate linkers (Huston J. S. et al., Proc. Natl. Acad. Sci. U.S.A. (1988) 85: 5879-5883). Specifically, such antibody fragments are generated by treating antibodies with an enzyme such as papain or pepsin. Alternatively, genes encoding these antibody fragments are constructed, inserted into expression vectors, and then expressed in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Antibodies linked to various molecules such as polyethylene glycol (PEG) or cytotoxic agents may be used as antibody modification products (Farmaco. 1999 Aug. 30; 54(8): 497-516; Cancer J. 2008 May-June; 14(3): 154-69). The antibodies used in the present invention also include such antibody modification products. Such antibody modification products can be obtained by chemically modifying antibodies. Such methods are already established in this field.

Antibodies to be used in the present invention include, but are not limited to, anti-tissue factor antibodies, anti-IL-6 receptor antibodies, anti-IL-6 antibodies, anti-glypican-3 antibodies, anti-CD3 antibodies, anti-CD20 antibodies, anti-GPIIb/IIIa antibodies, anti-TNF antibodies, anti-CD25 antibodies, anti-EGFR antibodies, anti-Her2/neu antibodies, anti-RSV antibodies, anti-CD33 antibodies, anti-CD52 antibodies, anti-IgE antibodies, anti-CD11a antibodies, anti-VEGF antibodies, anti-VLA4 antibodies, anti-HM1.24 antigen monoclonal antibodies, anti-parathyroid hormone-related peptide antibodies (anti-PTHrP antibodies), anti-ganglioside GM3 antibodies, anti-TPO receptor agonist antibodies, antibodies substituting for coagulation factor VIII, anti-IL31 receptor antibodies, anti-HLA antibodies, anti-AXL antibodies, anti-CXCR4 antibodies, anti-NR10 antibodies, and bi-specific antibodies against factor IX and factor X.

Preferred reshaped humanized antibodies used in the present invention include humanized anti-interleukin 6 (IL-6) receptor antibodies (tocilizumab, hPM-1, or MRA) (see WO 92/19759), humanized anti-HM1.24 antigen monoclonal antibodies (see WO 98/14580), humanized anti-parathyroid hormone-related peptide antibodies (anti-PTHrP antibodies) (see WO 98/13388), humanized anti-tissue factor antibodies (see WO 99/51743), anti-glypican-3 humanized IgG1κ antibodies (codrituzumab, GC33, see WO2006/006693), anti-NR10 humanized antibodies (see WO 2009/072604), and bi-specific humanized antibodies against factor IX and factor X (ACE910, see WO 2012/067176). Particularly preferred humanized antibodies used in the present invention are humanized anti-IL-6 receptor antibodies, anti-NR10 humanized antibodies, and bi-specific humanized antibodies against factor IX and factor X.

Preferred human IgM antibodies include recombinant human anti-ganglioside GM3 IgM antibodies (see WO 05/05636).

Preferred minibodies include anti-TPO receptor agonist diabodies (see WO 02/33072) and anti-CD47 agonist diabodies (see WO 01/66737).

Examples of antibodies used in the present invention include modified antibodies that show ion concentration-dependent (for example, pH-dependent or calcium ion concentration-dependent) antigen binding. Antibodies showing pH-dependent antigen binding, which strongly bind to an antigen under the neutral-pH range condition in plasma and dissociate from the antigen under the acidic-pH range condition in endosomes (antibodies that bind to an antigen under a neutral-pH range condition and dissociate from the antigen under an acidic-pH range condition); and antibodies showing calcium ion concentration-dependent antigen binding, which strongly bind to an antigen under the high-calcium ion concentration conditions in plasma and dissociate from the antigen under the low calcium ion concentration condition in endosomes (antibodies that bind to an antigen under a high-calcium ion concentration condition and dissociate from the antigen under a low-calcium ion concentration condition), can be dissociated from the antigen inside endosomes. When antibodies that show pH-dependent antigen binding and antibodies that show calcium ion concentration-dependent antigen binding are recycled into plasma by FcRn after antigen dissociation, they can bind again to antigens. Therefore, a single antibody molecule can repeatedly bind to multiple antigen molecules. Furthermore, through dissociation from antibodies in endosomes, antigens bound to the antigen-binding molecules are not recycled into plasma, and are degraded in lysosomes. Administering such antigen-binding molecules into a living body can promote intake of antigens into cells, and can decrease antigen concentration in plasma.

In the present invention, an antibody with low isoelectric point (low-pI antibody) refers particularly to an antibody having a low isoelectric point, which is difficult to find in nature. Examples of the isoelectric point of such an antibody include 3.0 to 8.0, preferably 5.0 to 7.5, more preferably 5.0 to 7.0, and particularly preferably 5.0 to 6.5, but are not limited thereto. It is thought that a naturally-occurring (or ordinary) antibody generally has an isoelectric point in the range of 7.5 to 9.5.

Furthermore, as an antibody used in the present invention, a pI-modified antibody whose pI has been reduced by altering the amino acid residues exposed on the surface of the antibody is preferred. Such a pI-modified antibody refers to an antibody whose pI has been reduced by 1 or more, preferably 2 or more, and more preferably 3 or more pI units in comparison to that of the antibody prior to the modification. As described below in the Examples, SA237 (Mab2 of the Examples of this application) whose isoelectric point is regulated by modifying the amino acid sequence of tocilizumab (isoelectric point: 9.4) has an isoelectric point of 5.8. Another example is a completely humanized NS22 antibody generated by the method of Example 12 of WO2009/072604, whose isoelectric point is regulated to be 5.6 through modifications of its amino acid sequence.

Antibodies with an improved isoelectric point include, for example, SA237 (Mab2, H chain/SEQ ID NO: 1; L chain/SEQ ID NO: 2), which is an anti-IL-6 receptor antibody described in WO 2009/041621, anti-NR10 humanized antibodies, and fully humanized NS22 antibodies produced by the method described in Example 12 of WO 2009/072604, but are not limited thereto.

In the case of an H-chain variable region, examples of amino acid residues exposed on the antibody surface include amino acid residues selected from among the amino acid residues at H1, H3, H5, H8, H10, H12, H13, H15, H16, H19, H23, H25, H26, H31, H39, H42, H43, H44, H46, H61, H62, H64, H65, H68, H71, H72, H73, H75, H76, H81, H82b, H83, H85, H86, H105, H108, H110, and H112 according to Kabat numbering, but are not limited thereto. In the case of an L-chain variable region, the examples are amino acid residues selected from among the amino acid residues at L1, L3, L7, L8, L9, L11, L12, L16, L17, L18, L20, L22, L24, L27, L38, L39, L41, L42, L43, L45, L46, L49, L53, L54, L55, L57, L60, L63, L65, L66, L68, L69, L70, L74, L76, L77, L79, L80, L81, L85, L100, L103, L105, L106, and L107 according to Kabat numbering, but are not limited thereto.

In the present invention, "modification" refers to substituting the original amino acid residue with another amino acid residue, deleting the original amino acid residue, adding a new amino acid residue, and such, but preferably, it refers to substitution of the original amino acid residue with another amino acid residue.

Some amino acids are known to be charged amino acids. Generally, lysine (K), arginine (R), and histidine (H) are known as positively charged amino acids (cationic amino acids). Aspartic acid (D), glutamic acid (E), and such are known as negatively charged amino acids (anionic amino acids). Amino acids other than these are known as uncharged amino acids.

In the present invention, preferably, the amino acid residues present after the modification are suitably selected from the amino acid residues included in either one of groups (a) and (b) below, without particular limitations thereto:

(a) glutamic acid (E) and aspartic acid (D); and
(b) lysine (K), arginine (R), and histidine (H).

In a preferred embodiment, if the amino acid residue before modification is already charged, it may be modified to be an uncharged amino acid residue.

More specifically, the modification in the present invention includes: (1) substitution of a charged amino acid with an uncharged amino acid; (2) substitution of a charged amino acid with an amino acid carrying a charge opposite to that of the original amino acid; and (3) substitution of an uncharged amino acid with a charged amino acid.

The value of an isoelectric point can be determined by isoelectric focusing known to those skilled in the art. Theoretical isoelectric point values can be calculated using a gene or amino acid sequence analysis software (for example, Genetyx).

Antibodies in which the charge of amino acid residues has been modified can be obtained by modifying nucleic acids encoding the antibodies, culturing those nucleic acids in host cells, and purifying the antibodies from the host cell culture. In the present invention, the phrase "modifying nucleic acids" refers to modifying nucleic acid sequences so that they become codons that correspond to amino acid residues introduced by the modification. More specifically, it refers to modifying the nucleotide sequence of a nucleic acid so that the codon encoding the original amino acid residue becomes a codon encoding the amino acid residue to be introduced by the modification. That is, a codon encoding the amino acid residue to be modified is replaced by a codon encoding the amino acid residue to be introduced by the modification. Such nucleic acid modifications can be carried out appropriately by those skilled in the art using known techniques, for example, site-directed mutagenesis or PCR mutagenesis.

Pharmaceutical compositions of the present invention may be liquid formulations (antibody-containing liquid formulations) or lyophilized formulations. Liquid formulations of the present invention include solutions before lyophilizing in the production process for lyophilized formulations, or solutions after redissolving. The liquid formulations of the present invention are preferably liquid formulations produced without including a lyophilizing step in the production process. Lyophilized agents of the present invention can be obtained by lyophilizing the liquid formulations of the present invention by methods known to those skilled in the art.

Formulations of the present invention can include additives such as cryoprotective agents, suspending agents, solubilizing agents, isotonizing agents, preservatives, adsorption-preventing agents, diluents, excipients, pH adjusters, analgesics, sulfur-containing reducing agents, and antioxidants, and carriers as necessary.

Examples of cryoprotective agents include, but are not limited to, sugars such as trehalose, sucrose, and sorbitol.

Examples of solubilizing agents include, but are not limited to, polyoxyethylene hydrogenated castor oil, Polysorbate 80, nicotinic acid amide, polyoxyethylene sorbitan monolaurate, macrogol, and castor oil fatty acid ethyl ester.

Examples of isotonizing agents include, but are not limited to, sodium chloride, potassium chloride, and calcium chloride.

Examples of preservatives include, but are not limited to, methyl p-hydroxybenzoate, ethyl p-hydroxybenzoate, sorbic acid, phenol, cresol, and chlorocresol.

Examples of adsorption-preventing agents include, but are not limited to, human serum albumin, lecithin, dextran, ethyleneoxide-propyleneoxide copolymer, hydroxypropyl cellulose, methylcellulose, polyoxyethylene hydrogenated castor oil, and polyethylene glycol.

Examples of sulfur-containing reducing agents include, but are not limited to, N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and compounds with sulfhydryl groups such as thioalkanoic acids that have one to seven carbon atoms.

Examples of antioxidants include, but are not limited to, erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium hydrogen sulfite, sodium sulfite, triamyl gallate, and propyl gallate, or chelating agents such as disodium ethylenediamine tetraacetate (EDTA), sodium pyrophosphate, and sodium metaphosphate.

A formulation of the present invention can be administered either orally or parenterally, but generally, it is administered via a parenteral route. Specifically, it is administered by injection, transdermal, transmucosal, transnasal, transpulmonary administration, or such. Examples of the types of injections include subcutaneous injection, intravenous injection, intramuscular injection, and such which enable systemic or local administration. In the case of subcutaneous injection, there is a limit to the amount of injection solution, but the amount of antibody administered per injection can be a large amount (100 mg to 200 mg or so). Therefore, formulations of the present invention are particularly suitable for use in subcutaneous administration (injection).

All prior art documents cited in the specification are incorporated herein by reference.

EXAMPLES

Herein below, the present invention will be described in further detail with reference to the Examples, but the scope of the invention is not limited to the Examples.

[Example 1] Correlation Between Particle Size Parameters and Viscosity for MAb1, MAb2, and MAb3

MAb1: a bispecific antibody that recognizes blood coagulation factor IX and/or activated blood coagulation factor IX, and blood coagulation factor X and/or activated blood coagulation factor X. ACE910 (Q499-z121/J327-z119/L404-k), which is a bispecific antibody described in a non-patent document (PLoS One. 2013; 8(2):e57479) and a patent document (WO 2012/067176) (a bispecific antibody in which the H chain comprising the amino acid sequence of SEQ ID NO: 3 and the L chain of SEQ ID NO: 5 are associated, and the H chain comprising the amino acid sequence of SEQ ID NO: 4 and the L chain of SEQ ID NO: 5 are associated), was prepared according to the description in the aforementioned non-patent document or the patent document. As described in the aforementioned patent document, ACE910 has an activity of substituting for the function of coagulation factor VIII.

MAb2: an anti-IL-6 receptor antibody described in WO 2009/041621, which is an antibody (SA237) whose pI value has been adjusted to 5.8 by modifying the amino acids of tocilizumab. The amino acid sequence of the MAb2 antibody is represented by H chain/SEQ ID NO: 1 and L chain/SEQ ID NO: 2.

MAb3: an anti-glypican 3 humanized antibody (GC33; general name: codrituzumab; an antibody that has been humanized by the method described in Example 24 of WO2006/006693, and whose L chain has been modified by the method of Example 25 of the same) which belongs to the IgG1 antibody class.

MAb1, MAb2, and MAb3 were used to prepare samples in which the antibody concentration is 60 mg/mL in the formulated solutions of Table 1. Capillary cells were filled with approximately 40 μL of the samples; and the particle size parameters, apparent particle radius of gyration $R_g^{app}$ (nm) and apparent maximum particle diameter $D_{max}^{app}$ (nm), were calculated using SAXSess mc² (Anton Paar). The results appear to show that the larger these values are, the higher the associativity of the antibodies. The experiment temperatures and the measurement results are shown in Table 1. Methods for calculating $R_g^{app}$ and $D_{max}^{app}$ are described below.

Method for Calculating $R_g^{app}$

1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as a variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Guinier plotting is performed on the scattering curves following absorption correction, blank correction, and desmearing correction; and $R_g^{app}$ is obtained under conditions that satisfy $q*R_g^{app}<1.3$.

Method for Calculating $D_{max}^{app}$

1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as a variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Pair distance distribution function (p(r)) of particles giving rise to the scattering is obtained by applying an indirect Fourier transform method (J Appl Cryst. 13:577-584 (1980)) to the scattering curves following absorption correction, blank correction, and desmearing correction. $D_{max}^{app}$ is obtained from the x-intercept of p(r).

Next, MAb1, MAb2, and MAb3 were used to prepare samples in which the antibody concentration is 200 mg/mL in the formulated solutions of Table 1. The viscosity η (mPa·s) of the samples was measured using 90 μL of the samples with an EMS viscometer (Kyoto Electronics Manufacturing Co., Ltd.) (J Artif Organs. 16:359-367 (2013)). The experiment temperatures and the measurement results are shown in Table 1.

TABLE 1

| MAb TYPE | FORMULATION | EXPERIMENT TEMPERATURE (° C.) | $R_g^{app}$ (nm) at 60 mg/mL | $D_{max}^{app}$ (nm) at 60 mg/mL | η (mPa · s) at 200 mg/mL |
|---|---|---|---|---|---|
| MAb1 | 5 mM citrate, 50 mM NaCl, NaOH (q.s.), pH 6.0 | 15 | 14.6 | 56 | 635.3 |
|  | 5 mM citrate, 50 mM NaCl, NaOH (q.s.), pH 6.0 | 20 | 12.6 | 49 | 355.7 |
|  | 5 mM citrate, 50 mM NaCl, NaOH (q.s.), pH 6.0 | 25 | 10.4 | 42 | 219.3 |
|  | 5 mM citrate, 50 mM NaCl, NaOH (q.s.), pH 6.0 | 30 | 10.1 | 39 | 131.0 |
|  | 5 mM citrate, 50 mM NaCl, NaOH (q.s.), pH 6.0 | 35 | 9.0 | 37 | 87.1 |
|  | 5 mM citrate, 150 mM NaCl, NaOH (q.s.), pH 6.0 | 25 | 6.8 | 28 | 34.6 |
|  | 20 mM His, 150 mM Arg, HCl (q.s.), pH 6.0 | 25 | 5.5 | 21 | 21.3 |
|  | 20 mM His, 150 mM Arg, Asp (q.s.), pH 6.0 | 25 | 4.9 | 17 | 17.0 |
| MAb2 | 5 mM citrate, 50 mM NaCl, NaOH (q.s.), pH 6.0 | 25 | 5.5 | 22 | 30.5 |
|  | 20 mM His, 150 mM Arg, Asp (q.s.), pH 6.0 | 25 | 5.2 | 20 | 23.6 |
| MAb3 | 5 mM citrate, 50 mM NaCl, NaOH (q.s.), pH 6.0 | 25 | 4.3 | 16 | 12.7 |
|  | 20 mM His, 150 mM Arg, Asp (q.s.), pH 6.0 | 25 | 3.8 | 14 | 9.8 |

Figure 2:
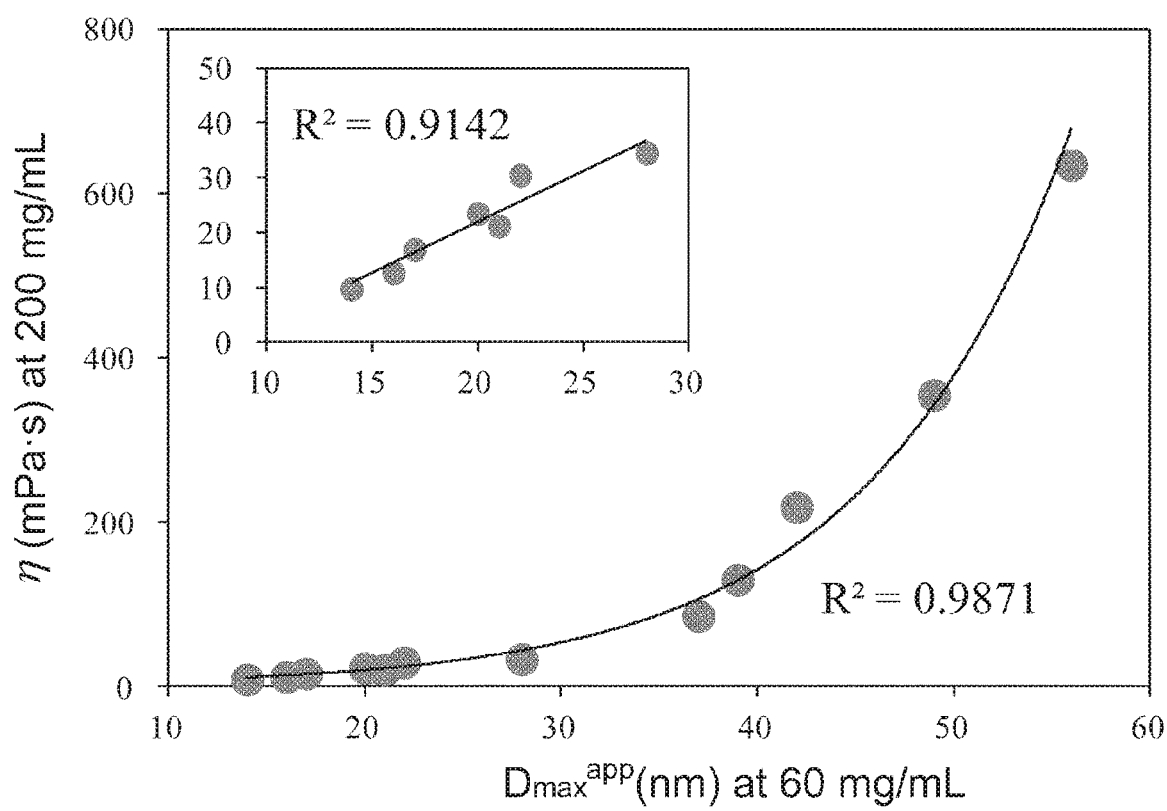
FIG. 2 is a graph showing the result of plotting the viscosity of each antibody solution obtained as a function of $D_{max}^{app}$ at 60 mg/mL and at 15° C. to 35° C. from SAXS measurements.

To investigate a correlation between the particle size parameters ($R_g^{app}$ and $D_{max}^{app}$) at 60 mg/mL obtained from SAXS measurements and the viscosities (measured values) at 200 mg/mL, the viscosities of MAb1, MAb2, and MAb3 were plotted as a function of $R_g^{app}$ or $D_{max}^{app}$, and the results are shown in FIGS. 1 and 2. Excellent correlations with viscosity were observed for both of the particle size parameters. The correlation fit well exponentially, and linear correlation was observed in the low viscosity range. The above showed that even without an actual measurement of viscosity which requires high-concentration samples for the measurement, the viscosity at high concentration can be predicted by using $R_g^{app}$ or $D_{max}^{app}$ as an indicator, which can be obtained from SAXS measurements using low-concentration samples.

[Example 2] Correlation of Viscosity with Particle Size Parameters and Molecular Weight Parameters for MAb1, MAb3, and MAb4

MAb1, MAb3 (both are the same as those described in Example 1), and MAb4 (humanized anti-IL-6 receptor antibody; generic name: tocilizumab) were used to prepare samples in which the antibody concentration is 15 mg/mL in the formulated solutions of Table 2. Microcapillary cells were filled with approximately 10 μL of the samples; and the particle size parameters, which are the apparent particle radius of gyration $R_g^{app}$ (nm) and the apparent maximum particle diameter $D_{max}^{app}$ (nm), as well as the scattering intensity I(0) (a.u.) at zero scattering angle as a value proportional to the apparent molecular weight were calculated using SAXSess mc² (Anton Paar). The results appear to show that the larger these values are, the higher the associativity of the antibodies. In order to more clearly detect the difference in associativity between the samples, measurements were taken at a low temperature of 5° C. The measurement results are shown in Table 2. Methods for calculating 40), $R_g^{app}$, and $D_{max}^{app}$ are described below.

Method for Calculating I(0) and $R_g^{App}$
1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as a variable.
3) The scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Guinier plotting is performed on the scattering curves following absorption correction, blank correction, and desmearing correction, and $R_g^{app}$ is obtained under conditions that satisfy $q*R_g^{app}<1.3$. At the same time, I(0) is obtained from the y intercept.

Method for Calculating $D_{max}^{App}$
1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as a variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Pair distance distribution function (p(r)) of particles giving rise to the scattering is obtained by applying an indirect Fourier transform method (J Appl Cryst. 13:577-584 (1980)) to the scattering curves following absorption correction, blank correction, and desmearing correction. $D_{max}^{app}$ is obtained from the x intercept of p(r).

Next, MAb1, MAb3, and MAb4 were used to prepare samples in which the antibody concentration is 160 mg/mL in the formulated solutions of Table 2. The viscosity η (mPa·s) of the samples was measured using 90 μL of the samples with an EMS viscometer (Kyoto Electronics Manufacturing Co., Ltd.) (J Artif Organs. 16:359-367 (2013)). The experiment temperature was set to 25° C. The measurement results are shown in Table 2.

TABLE 2

| MAb TYPE | FORMULATION | I(0) (a.u.) at 15 mg/mL, 5° C. | $R_g^{app}$ (nm) at 15 mg/mL, 5° C. | $D_{max}^{app}$ (nm) at 15 mg/mL, 5° C. | η (mPa·s) at 160 mg/mL, 25° C. |
|---|---|---|---|---|---|
| MAb1 | 5 mM citrate, 150 mM NaCl, NaOH (q.s.), pH 6.0 | 7.2 | 6.5 | 27 | 12.4 |
| MAb1 | 5 mM citrate, 180 mM NaCl, NaOH (q.s.), pH 6.0 | 6.5 | 5.9 | 24 | 11.4 |
| MAb1 | 20 mM His, 150 mM Arg, HCl (q.s.), pH 6.0 | 5.7 | 5.4 | 19 | 8.5 |
| MAb1 | | 5.0 | 5.1 | 19 | 7.5 |
| MAb3 | 20 mM His, 150 mM Arg, Asp (q.s.), pH 6.0 | 3.9 | 4.8 | 16 | 5.4 |
| MAb4 | | 4.0 | 4.9 | 16 | 6.2 |

Figure 3:
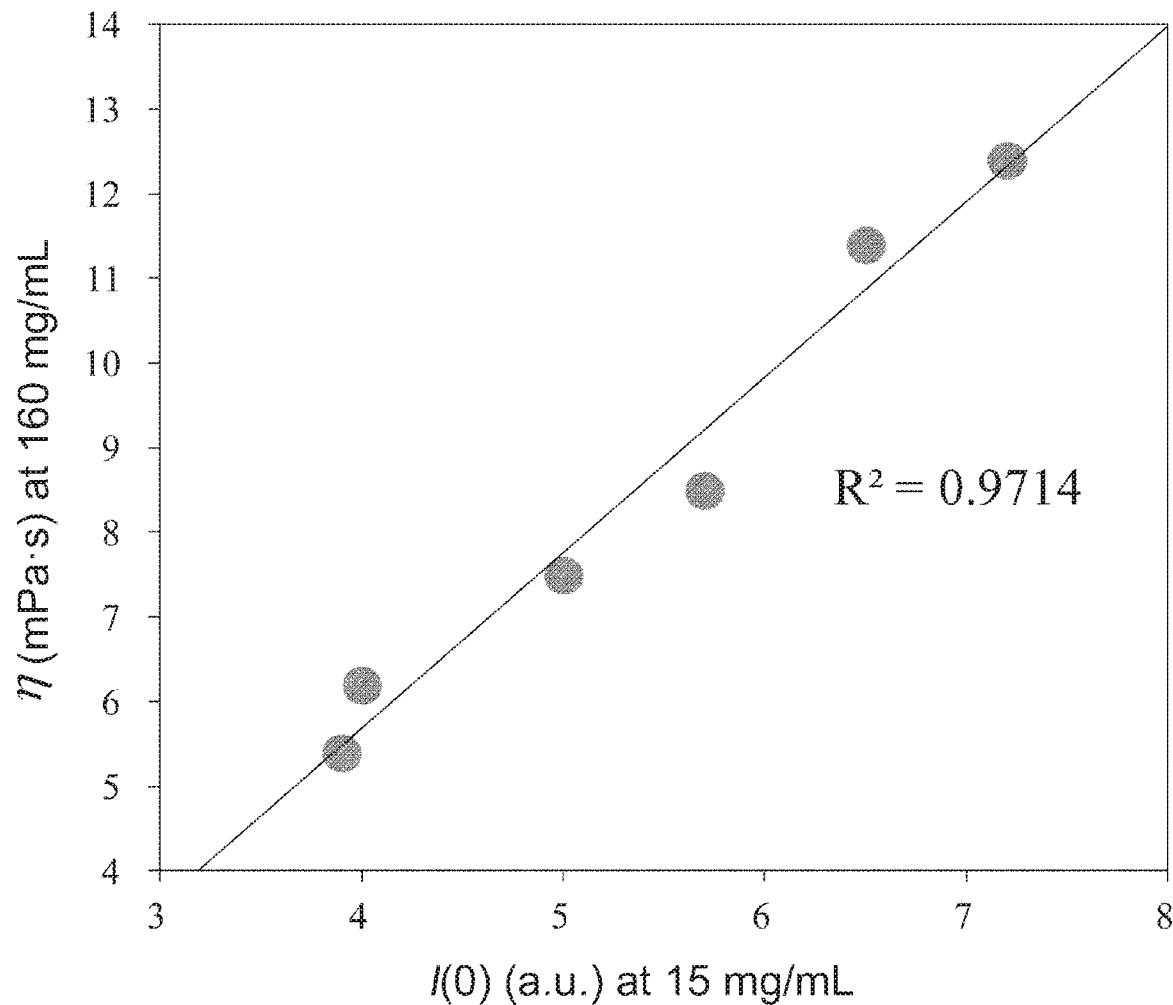
FIG. 3 is a graph showing the result of plotting the viscosity of each antibody solution obtained as a function of I(0) at 15 mg/mL and at 5° C. from SAXS measurements.
Figure 4:
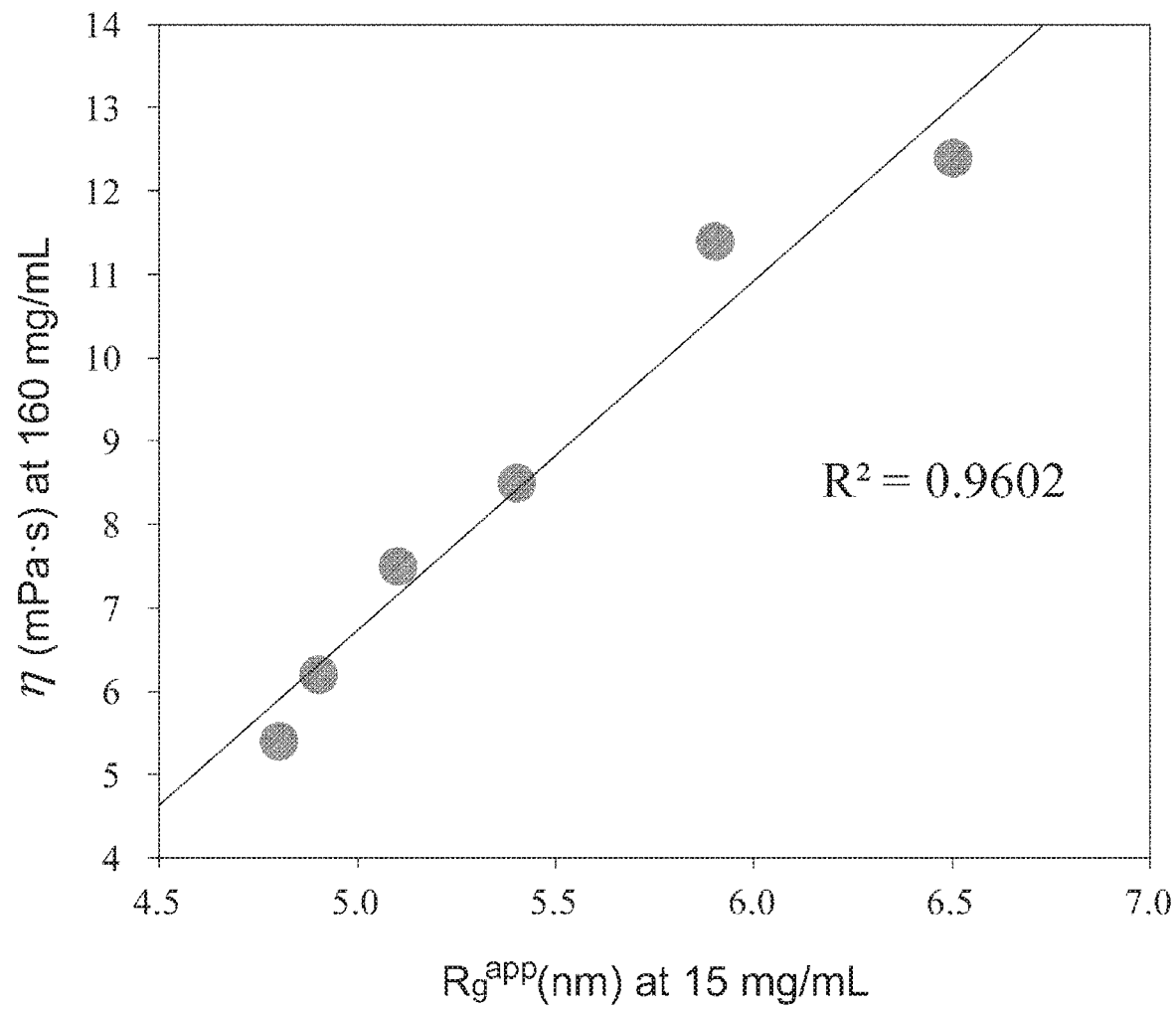
FIG. 4 is a graph showing the result of plotting the viscosity of each antibody solution obtained as a function of $R_g^{app}$ at 15 mg/mL and at 5° C. from SAXS measurements.
Figure 5:
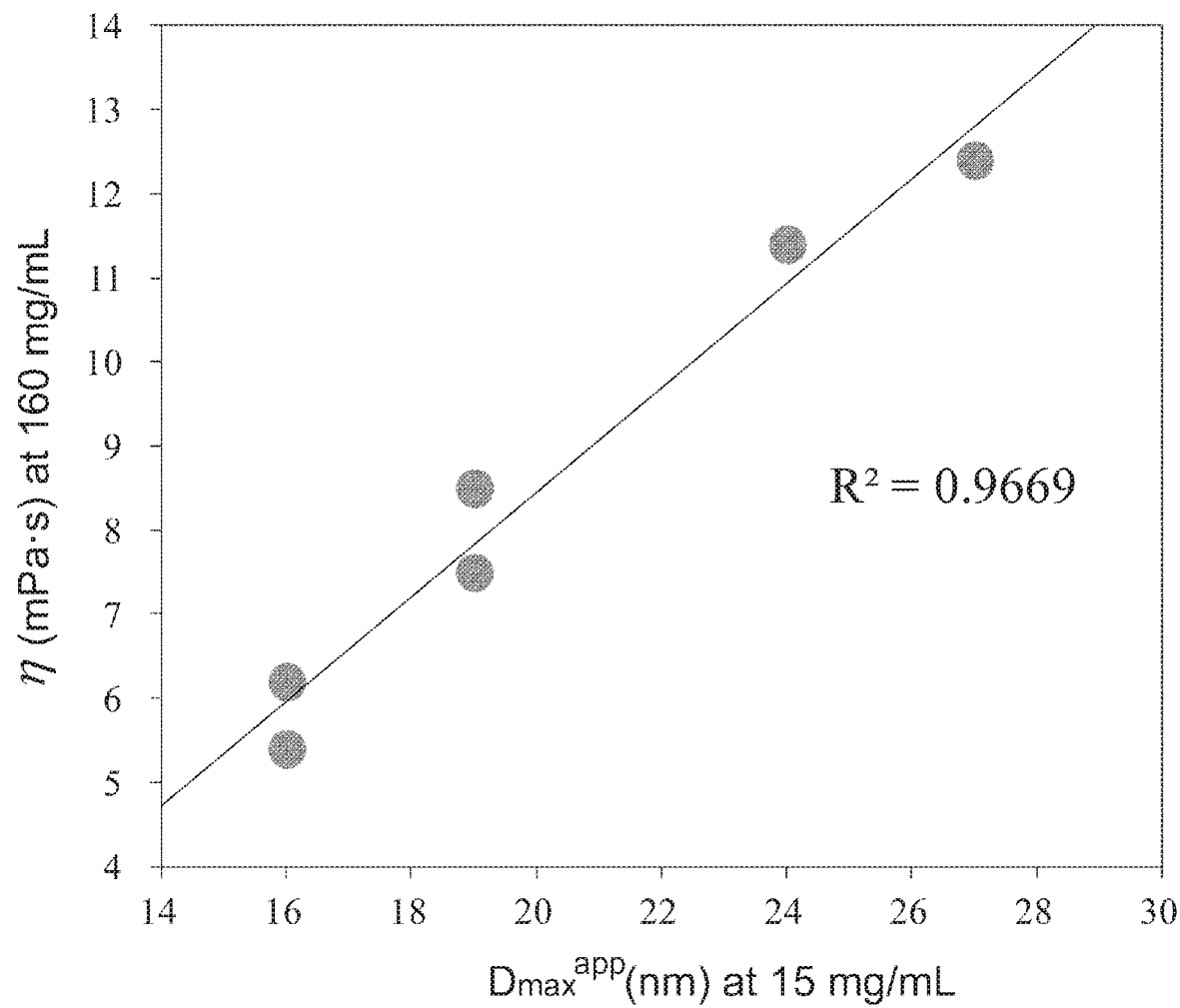
FIG. 5 is a graph showing the result of plotting the viscosity of each antibody solution obtained as a function of $D_{max}^{app}$ at 15 mg/mL and at 5° C. from SAXS measurements.

To investigate a correlation between the particle size parameters (I(0), $R_g^{app}$, and $D_{max}^{app}$) at 5° C. and 15 mg/mL obtained from SAXS measurements, and the viscosity at 25° C. and 160 mg/mL, the viscosities of MAb1, MAb3, and MAb4 were plotted as a function of I(0), $R_g^{app}$, or $D_{max}^{app}$, and the results are shown in FIGS. 3, 4, and 5. Excellent correlations with viscosity were observed for all of the above particle size parameters. Therefore, it has been shown that even without an actual measurement of viscosity which requires samples in large amounts and at high concentrations for the measurement, the viscosity at a high concentration can be predicted by using particle size parameters as an indicator, which can be obtained from SAXS measurements using samples in small amounts and at low concentrations.

Furthermore, when preparing various modified proteins in which a portion of the amino acid sequence of a protein such as an antibody is substituted with different amino acids, and selecting viscosity-controlled modified proteins, similar excellent correlations are also observed for the measured values of viscosity and parameters obtainable by the methods of the present invention. Therefore, the methods of the present invention are also useful as methods for selecting desired viscosity-regulated modified proteins.

[Example 3] Correlation Between Particle Size Parameters and Viscosity for MAb2 and MAb4

MAb2 and MAb4 (same as in Example 1 and Example 2, respectively) were used to examine whether differences in viscosity between the antibody prior to amino acid sequence modification (Mab4) and the antibody in which a portion of the amino acid sequence has been substituted with other amino acids (Mab2) can be evaluated using the measurement methods of the present invention. The respective antibodies were used to prepare samples in which the antibody concentration is 15 mg/mL in the formulated solutions of Table 3. Microcapillary cells were filled with approximately 10 μL of the samples, and the particle size parameters, which are scattering intensity I(0) at zero scattering angle, apparent particle radius of gyration $R_g^{app}$, and apparent maximum particle diameter $D_{max}^{app}$ (nm), were calculated using SAXSess mc² (Anton Paar). The results appear to show that the larger these values are, the higher the associativity of the antibodies. In order to more clearly detect the difference in association properties between the samples, measurements were taken at a low temperature of 5° C. The measurement results are shown in Table 3. Methods for calculating I(0), $R_g^{app}$, and $D_{max}^{app}$ are described below.

Method for Calculating I(0) and $R_g^{App}$

1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as the variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Guinier plotting is performed on the scattering curves following absorption correction, blank correction, and desmearing correction, and $R_g^{app}$ is obtained under conditions that satisfy $q*R_g^{app}<1.3$. At the same time, I(0) is obtained from the y intercept.

Method for Calculating $D_{max}^{App}$

1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as the variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Pair distance distribution function (p(r)) of particles giving rise to the scattering is obtained by applying an indirect Fourier transform method (J Appl Cryst. 13:577-584 (1980)) to the scattering curves following absorption correction, blank correction, and desmearing correction. $D_{max}^{app}$ is obtained from the x intercept of p(r).

Next, MAb2 and MAb4 were used to prepare samples in which the antibody concentration is 160 mg/mL in the formulated solutions of Table 3. The viscosity η (mPa·s) of the samples was measured using 90 μL of the samples with an EMS viscometer (Kyoto Electronics Manufacturing Co., Ltd.) (J Artif Organs. 16:359-367 (2013)). The experiment temperature was set to 25° C. The measurement results are shown in Table 3.

The particle size parameters (I(0), $R_g^{app}$, and $D_{max}^{app}$) at 15 mg/mL and 5° C. obtained through SAXS measurements, and the viscosity at 160 mg/mL and 25° C. were confirmed to be definitely correlated. This proved the validity of the method of screening for amino acid-substituted proteins with viscosity as an indicator by using the method of the present invention.

[Example 4] Correlation Between Particle Size Parameters and Viscosity for MAb1, MAb2, MAb3, MAb4, and BSA MAb1, MAb2, MAb3, MAb4 (all of them are the same as those of Examples 1 to 2), and BSA were used to prepare samples in which the protein concentration is 15 mg/mL in the formulated solutions of Table 4. Microcapillary cells were filled with approximately 10 μL of the samples, and the particle size parameters, which are scattering intensity I(0) at zero scattering angle, apparent particle radius of gyration $R_g^{app}$, and apparent maximum particle diameter $D_{max}^{app}$ (nm), were calculated using SAXSess mc² (Anton Paar). These values appear to represent the particle size of the proteins taking into account the state of association. In order to more clearly detect the difference in associativity between the samples, measurements were taken at a low temperature of 5° C. The measurement results are shown in Table 3. Methods for calculating I(0), $R_g^{app}$, and $D_{max}^{app}$ are described below.

Method for Calculating I(0) and $R_g^{app}$

1) Scattering patterns of the samples and the solvent (blank) are detected by using a two-dimensional imaging plate.
2) Scattering curves are obtained by using a SAXSQuant software (Anton Paar) to transform the two-dimensional scattering patterns into one-dimensional scattering intensities with scattering vector q as the variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Guinier plotting is performed on the scattering curves following absorption correction, blank correction, and desmearing correction, and $R_g^{app}$ is obtained under conditions that satisfy $q*R_g^{app}<1.3$. At the same time, I(0) is obtained from the y intercept.

Method for Calculating $D_{max}^{app}$

1) Scattering patterns of the samples and the solvent (blank) are detected by using a two-dimensional imaging plate.
2) Scattering curves are obtained by using the SAXSQuant software (Anton Paar) to transform the two-dimensional scattering patterns into one-dimensional scattering intensities with scattering vector q as the variable.
3) Scattering curves are normalized with the scattering intensities at q=0 upon transmission through a beam stopper.
4) The scattering curve of the blank is subtracted from the scattering curves of the samples (blank correction).
5) Desmearing correction (optical correction) is performed.
6) Pair distance distribution function (p(r)) of particles giving rise to the scattering is obtained by applying an indirect Fourier transform method (J Appl Cryst. 13:577-584 (1980)) to the scattering curves following absorption correction, blank correction, and desmearing correction. $D_{max}^{app}$ is obtained from the x intercept of p(r).

Next, MAb1, MAb2, MAb3, MAb4, and BSA were used to prepare samples in which the protein concentration is 160 mg/mL in the formulated solutions of Table 4. The viscosity

TABLE 3

| MAbTYPE | FORMULATION | I(0) (a.u.) at 15 mg/mL, 5° C. | $R_g^{app}$ (nm) at 15 mg/mL, 5° C. | $D_{max}^{app}$ (nm) at 15 mg/mL, 5° C. | η (mPa·s) at 160 mg/mL, 25° C. |
|---|---|---|---|---|---|
| MAb2 | 20 mM His, 150 mM Arg, Asp (q.s.), pH 6.0 | 5.5 | 5.8 | 22 | 9.8 |
| MAb4 | | 4.0 | 4.9 | 16 | 6.2 |

η (mPa·s) of the samples was measured using 90 μL of the samples with an EMS viscometer (Kyoto Electronics Manufacturing Co., Ltd.) (J Artif Organs. 16:359-367 (2013)). The experiment temperature was set to 25° C. The measurement results are shown in Table 4.

The particle size parameters (I(0), $R_g^{app}$, and $D_{max}^{app}$) at 15 mg/mL and 5° C. obtained through SAXS measurements, and the viscosity at 160 mg/mL and 25° C. were confirmed to be definitely correlated, and this proved that the method of the present invention for evaluating viscosity can be applied to proteins other than antibodies.

TABLE 4

| MAb TYPE | FORMULATION | I(0) (a.u.) at 15 mg/mL, 5° C. | $R_g^{app}$ (nm) at 15 mg/mL, 5° C. | $D_{max}^{app}$ (nm) at 15 mg/mL, 5° C. | η (mPa · s) at 160 mg/mL, 25° C. |
|---|---|---|---|---|---|
| MAb1 | 20 mM His, 150 mM Arg, Asp (q.s.), pH 6.0 | 5.0 | 5.1 | 19 | 7.5 |
| MAb2 | | 5.5 | 5.8 | 22 | 9.8 |
| MAb3 | | 3.9 | 4.8 | 16 | 5.4 |
| MAb4 | | 4.0 | 4.9 | 16 | 6.2 |
| BSA | | 2.1 | 2.9 | 8 | 3.0 |

[Example 5] Correlation Between Particle Size Parameters and Viscosity for MAb5 and its Modified Antibodies The viscosities of MAb5 (anti-IgE antibody) and MAb5-A which is a modified antibody produced by substituting four amino acid residues at specified positions in MAb5 with histidine were measured. The residues before and after the modification are shown in Table 5. The positions of modification shown in Table 5 are indicated based on Kabat numbering. Samples were prepared with a protein concentration of 151 mg/mL or 155 mg/mL in the formulated solutions of Table 6. The viscosity η (mPa·s) of the samples were measured using 90 μL of the samples with an EMS viscometer (Kyoto Electronics Manufacturing Co., Ltd.) (J Artif Organs. 16:359-367 (2013)). The experiment temperature was set to 25° C. The measurement results are shown in Table 6. Large increase in viscosity was observed as a result of the substitution of four residues with histidine.

To identify the modification that causes this increase in viscosity and to design modified antibodies with low viscosity, MAb5, MAb5-A, and four modified antibodies (MAb5-B, MAb5-C, MAb5-D, and MAb5-E) produced by restoring the residues of MAb5 one at a time at the four residues substituted with histidine in MAb5-A were used to prepare samples in which the protein concentration is 30 mg/mL in the formulated solutions of Table 6. The residues before and after the modifications are shown in Table 5. Microcapillary cells were filled with approximately 10 μL of the samples, and the apparent maximum particle diameter $D_{max}^{app}$ (nm) was calculated using SAXSess mc² (Anton Paar). This value appears to represent the particle size of the protein, taking into account the state of association. In order to more clearly detect the difference in associativity between the samples, measurements were taken at a low temperature of 5° C. The measurement results are shown in Table 6. The $D_{max}^{app}$ values of MAb5-A, MAb5-B, MAb5-D, and MAb5-E were clearly larger than the $D_{max}^{app}$ value of MAb5 before modification, and the $D_{max}^{app}$ value of MAb5-C was 21 nm which is a value close to the $D_{max}^{app}$ value of MAb5 prior to modification. This MAb5-C was used to prepare a sample in which the protein concentration is 160 mg/mL, and when the viscosity η (mPa·s) of the sample at 25° C. was measured similarly to the case with Mab5 and Mab5-A, the result was 10.4 mPa·s which is a value close to the viscosity of MAb5 prior to modification. This strongly suggested that the modification which substitutes proline at a specified position with histidine causes an increase in viscosity. As such, it has been shown that measuring the apparent particle size using the small angle X-ray scattering (SAXS) method or the X-ray solution scattering method enables efficient selection of proteins with regulated viscosity (low viscosity) using a small amount of sample, and efficient production of such proteins. A method for calculating $D_{max}^{app}$ is described below.

Method for Calculating $D_{max}^{app}$

1) Scattering patterns of the samples and the solvent (blank) are detected by using a two-dimensional imaging plate.

2) Scattering curves are obtained by using the SAXSQuant software (Anton Paar) to transform the two-dimensional scattering patterns into one-dimensional scattering intensities with scattering vector q as the variable.

3) Scattering curves are normalized with the scattering intensities at q=0 upon transmission through a beam stopper.

4) The scattering curve of the blank is subtracted from the scattering curves of the samples (blank correction).

5) Desmearing correction (optical correction) is performed.

6) Pair distance distribution function (p(r)) of particles giving rise to the scattering is obtained by applying an indirect Fourier transform method (J Appl Cryst. 13:577-584 (1980)) to the scattering curves following absorption correction, blank correction, and desmearing correction. $D_{max}^{app}$ is obtained from the x intercept of p(r).

The SAXS screening method suggested the possibility that viscosity can be reduced by further modification of MAb5-A to MAb5-C. Therefore, the viscosity of MAb5-C was actually measured by the above-described measurement method. The measurement result for MAb5-C at the protein concentration of 160 mg/mL is shown in Table 6. Large decrease in viscosity was clearly observed, and this proved the validity of the present screening method.

Figure 6:
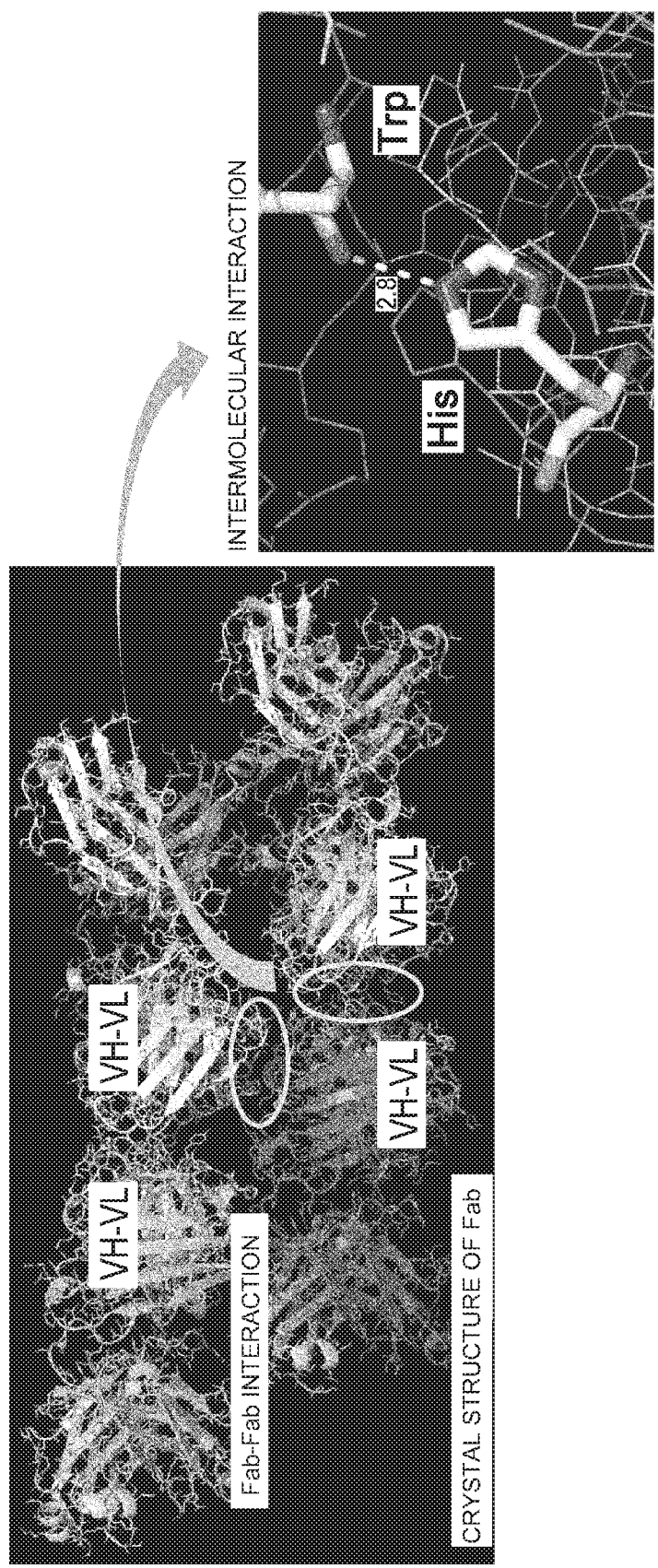
FIG. 6 shows a crystal structure of Fab in Mab5-A. The Fab-Fab interaction in Mab5-A is shown on the left. The right panel is a magnified view of the portion enclosed in the oval shown in the left panel, and shows that His at position 97 in one of the major Fab chains is at a distance capable of forming a hydrogen bond with the other major Fab chain.

Furthermore, the crystal structure of Fab in Mab5-A is shown in FIG. 6. In FIG. 6, the left panel shows that the Mab5-A molecules interact with each other via the Fab domains, and the right panel shows that the side chain of His at position 97 in the Fab domain of the Mab5-A molecule exists at a distance where it can form a hydrogen bond with the main chain of Trp in the Fab domain of the other Mab5-A molecule. On the other hand, in Mab5, such an Fab-Fab interaction is not observed. Therefore, increase in viscosity as a result of substitution of His for Pro at position 97 in Mab5 may be caused by formation of a hydrogen bond between different Fabs due to this substitution. As such, the results of crystal structure analysis also suggested validity of this screening method.

TABLE 5

| MAb TYPE | POSITION OF MODIFICATION AND MODIFIED AMINO ACID RESIDUE | | | |
|---|---|---|---|---|
| | 57 | 97 | 98 | 102 |
| MAb5 | Thr | Pro | Ser | Ile |
| MAb5-A | His | His | His | His |
| MAb5-B | Thr | His | His | His |
| MAb5-C | His | Pro | His | His |
| MAb5-D | His | His | Ser | His |
| MAb5-E | His | His | His | Ile |

TABLE 6

| MAb TYPE | FORMULATION | $D_{max}^{app}$ (nm) at 30 mg/mL, 5° C. | $\eta$ (mPa·s) at 25° C. |
|---|---|---|---|
| MAb5 | 20 mM His, 150 mM Arg, Asp (q.s.), pH 6.0 | 19 | 6.4 (151 mg/mL) |
| MAb5-A | | 31 | 32.3 (155 mg/mL) |
| MAb5-B | | 28 | — |
| MAb5-C | | 21 | 10.4 (160 mg/mL) |
| MAb5-D | | 32 | — |
| MAb5-E | | 36 | — |

INDUSTRIAL APPLICABILITY

The present invention has provided methods that enable convenient measurement of viscosity of a protein solution using a small amount of sample. The present invention facilitates the development of protein solution formulations with low viscosity, and enables selection (screening) of proteins having low viscosity in solution; and thus it enables provision of solution formulations of proteins such as antibodies with excellent physical properties. The methods of the present invention are particularly useful in producing low-viscosity biopharmaceuticals.

The invention claimed is:

1. A method of determining viscosity, at a given temperature, of a protein solution of interest having a given concentration of a protein that is between 1 mg/mL and 100 mg/mL, inclusive, the method comprising:
   (a) irradiating, at the given temperature, a sample of the protein solution of interest with X-ray to obtain a scattering pattern;
   (b) determining, from the scattering pattern, a value for a parameter selected from: apparent maximum particle diameter ($D_{max}^{app}$) of the protein in the sample, apparent particle radius of gyration ($R_g^{app}$) of the protein in the sample, and apparent molecular weight of the protein in the sample; and
   (c) using the value for the selected parameter to determine, from a predetermined calibration curve, viscosity at the given temperature of the protein solution of interest, wherein the predetermined calibration curve correlates:
      (i) viscosity, measured at the given temperature, of a sample of each of a plurality of different test solutions, each comprising a test protein at the given concentration, to
      (ii) a value for the selected parameter of each of the test solutions, measured at the given temperature;
   wherein the test proteins in the test solutions are the same or different.

2. The method of claim 1, wherein the given concentration is between 10 mg/mL and 100 mg/mL, inclusive.

3. The method of claim 1, wherein the given concentration is between 10 mg/mL and 30 mg/mL, inclusive.

4. The method of claim 1, wherein the given concentration is between 15 mg/mL and 30 mg/mL, inclusive.

5. The method of claim 1, wherein the given temperature is between 0° C. and 40° C., inclusive.

6. The method of claim 1, wherein the given temperature is between 0° C. and 25° C., inclusive.

7. The method of claim 1, wherein the given temperature is between 3° C. and 10° C., inclusive.

8. The method of claim 1, wherein the sample of the protein solution of interest has a volume of 1 µL to 100 µL.

9. The method of claim 1, wherein the sample of the protein solution of interest has a volume of 5 µL to 30 µL.

10. The method of claim 1, wherein the protein in the protein solution of interest is an antibody.

11. A method of selecting a protein that possesses desired viscosity characteristics, the method comprising:
   (A) providing a solution comprising a given protein;
   (B) carrying out the method of claim 1, wherein the solution of (A) is the protein solution of interest, thereby determining the viscosity of the protein solution of interest at the given temperature;
   (C) determining that the viscosity of the protein solution of interest at the given temperature is a desired viscosity; and
   (D) selecting the given protein as possessing the desired viscosity characteristics.

12. A method of producing a protein that possesses desired viscosity characteristics, the method comprising:
   (A) selecting an original protein;
   (B) producing a second protein that is a mutated version of the original protein;
   (C) preparing a solution comprising the second protein;
   (D) carrying out the method of claim 1, using the solution of (C) as the protein solution of interest, thereby determining the viscosity of the protein solution of interest at the given temperature;

(E) determining that the viscosity of the protein solution of interest at the given temperature is a desired viscosity, thereby determining that the second protein is a protein that possesses the desired viscosity characteristics.

13. The method of claim 12, wherein the desired viscosity is 2000 mPa·s or less.

14. The method of claim 12, wherein the desired viscosity is between 0.1 mPa·s and 1000 mPa·s, inclusive.

15. The method of claim 12, wherein the desired viscosity is between 0.1 mPa·s and 700 mPa·s, inclusive.

16. The method of claim 12, wherein the viscosity of the protein solution of interest is lower than the viscosity of a reference protein solution, wherein the reference protein solution is identical to the protein solution of interest except that the reference protein solution comprises the original protein instead of the second protein.

17. The method of claim 12, wherein the original protein comprises a first amino acid sequence and the second protein comprises a second amino acid sequence, and the first and second amino acid sequences are identical except that the second amino acid sequence comprises histidine (His) at one or more positions that are not His in the first amino acid sequence.

18. The method of claim 12, wherein the original protein is an antibody.

19. The method of claim 18, wherein the original protein comprises a first antibody heavy chain amino acid sequence and the second protein comprises a second antibody heavy chain amino acid sequence, and the second antibody heavy chain amino acid sequence has an amino acid residue other than His at Kabat numbering position 97.

20. The method of claim 18, wherein the original protein comprises a first antibody heavy chain amino acid sequence and the second protein comprises a second antibody heavy chain amino acid sequence, and the first and second antibody heavy chain amino acid sequences have an identical amino acid residue at Kabat numbering position 97.

21. The method of claim 18, wherein the second protein is an ion concentration-dependent antigen binding antibody.

22. A method of determining viscosity, at a first temperature, of a protein solution of interest having a given concentration of a protein that is between 1 mg/mL and 100 mg/mL, inclusive, the method comprising:
(a) irradiating, at a second temperature, a sample of the protein solution of interest with X-ray to obtain a scattering pattern;
(b) determining, from the scattering pattern, a value for a parameter selected from: apparent maximum particle diameter ($D_{max}^{app}$) of the protein in the sample, apparent particle radius of gyration ($R_g^{app}$) of the protein in the sample, and apparent molecular weight of the protein in the sample; and
(c) using the value for the selected parameter to determine, from a predetermined calibration curve, viscosity at the first temperature of the protein solution of interest, wherein the predetermined calibration curve correlates:
(i) viscosity, measured at the first temperature, of a sample of each of a plurality of different test solutions, each comprising a test protein at the given concentration, to
(ii) a value for the selected parameter of each of the test solutions, measured at the second temperature;
wherein the test proteins in the test solutions are the same or different.

23. The method of claim 22, wherein the given concentration is between 10 mg/mL and 100 mg/mL, inclusive.

24. The method of claim 22, wherein the given concentration is between 10 mg/mL and 30 mg/mL, inclusive.

25. The method of claim 22, wherein the given concentration is between 15 mg/mL and 30 mg/mL, inclusive.

26. The method of claim 22, wherein the second temperature is between 0° C. and 40° C., inclusive.

27. The method of claim 22, wherein the second temperature is between 0° C. and 25° C., inclusive.

28. The method of claim 22, wherein the second temperature is between 3° C. and 10° C., inclusive.

29. The method of claim 22, wherein the sample of the protein solution of interest has a volume of 1 µL to 100 µL.

30. The method of claim 22, wherein the sample of the protein solution of interest has a volume of 5 µL to 30 µL.

31. The method of claim 22, wherein the protein in the protein solution of interest is an antibody.

32. A method of selecting a protein that possesses desired viscosity characteristics, the method comprising:
(A) providing a solution comprising a given protein;
(B) carrying out the method of claim 22, wherein the solution of (A) is the protein solution of interest, thereby determining the viscosity of the protein solution of interest at the first temperature;
(C) determining that the viscosity of the protein solution of interest at the first temperature is a desired viscosity; and
(D) selecting the given protein as possessing the desired viscosity characteristics.

33. A method of producing a protein that possesses desired viscosity characteristics, the method comprising:
(A) selecting an original protein;
(B) producing a second protein that is a mutated version of the original protein;
(C) preparing a solution comprising the second protein;
(D) carrying out the method of claim 22, using the solution of (C) as the protein solution of interest, thereby determining the viscosity of the protein solution of interest at the first temperature;
(E) determining that the viscosity of the protein solution of interest at the first temperature is a desired viscosity, thereby determining that the second protein is a protein that possesses the desired viscosity characteristics.

34. The method of claim 33, wherein the desired viscosity is 2000 mPa·s or less.

35. The method of claim 33, wherein the desired viscosity is between 0.1 mPa·s and 1000 mPa·s, inclusive.

36. The method of claim 33, wherein the desired viscosity is between 0.1 mPa·s and 700 mPa·s, inclusive.

37. The method of claim 33, wherein the viscosity of the protein solution of interest is lower than the viscosity of a reference protein solution, wherein the reference protein solution is identical to the protein solution of interest except that the reference protein solution comprises the original protein instead of the second protein.

38. The method of claim 33, wherein the original protein comprises a first amino acid sequence and the second protein comprises a second amino acid sequence, and the first and second amino acid sequences are identical except that the second amino acid sequence comprises His at one or more positions that are not His in the first amino acid sequence.

39. The method of claim 33, wherein the original protein is an antibody.

40. The method of claim 39, wherein the original protein comprises a first antibody heavy chain amino acid sequence and the second protein comprises a second antibody heavy chain amino acid sequence, and the second antibody heavy chain amino acid sequence has an amino acid residue other than His at Kabat numbering position 97.

41. The method of claim 39, wherein the original protein comprises a first antibody heavy chain amino acid sequence and the second protein comprises a second antibody heavy chain amino acid sequence, and the first and second antibody heavy chain amino acid sequences have an identical amino acid residue at Kabat numbering position 97.

42. The method of claim 39, wherein the second protein is an ion concentration-dependent antigen binding antibody.

43. A method of predicting viscosity, at a given temperature, of a protein solution of interest having a first concentration of a protein, the method comprising:
   (a) irradiating, at the given temperature, a sample solution having a second concentration of the protein with X-ray to obtain a scattering pattern, wherein the sample solution and the protein solution of interest are identical except for protein concentration;
   (b) determining, from the scattering pattern, a value for a parameter selected from: apparent maximum particle diameter ($D_{max}^{app}$) of the protein in the sample solution, apparent particle radius of gyration ($R_g^{app}$) of the protein in the sample solution, and apparent molecular weight of the protein in the sample solution; and
   (c) using the value for the selected parameter to determine, from a predetermined calibration curve, viscosity at the given temperature of the protein solution of interest,
      wherein the predetermined calibration curve correlates, for each of a plurality of test solution/corresponding solution pairs:
   (i) a value for the selected parameter, measured at the given temperature, for the test solution, to
   (ii) viscosity, measured at the given temperature, of the corresponding solution,
      wherein each test solution comprises a test protein that is the same or varies among the plurality of test solutions,
      wherein each test solution and its paired corresponding solution comprise the same test protein and are identical except for concentration of the test protein,
      wherein the concentration of test protein in all of the test solutions is the second concentration and the concentration of test protein in all of the corresponding solutions is the first concentration, and
      wherein the second concentration is between 1 mg/mL and 100 mg/mL, inclusive.

44. The method of claim 43, wherein the second concentration is between 10 mg/mL and 100 mg/mL, inclusive.

45. The method of claim 43, wherein the second concentration is between 10 mg/mL and 30 mg/mL, inclusive.

46. The method of claim 43, wherein the second concentration is between 15 mg/mL and 30 mg/mL, inclusive.

47. The method of claim 43, wherein the given temperature is between 0° C. and 40° C., inclusive.

48. The method of claim 43, wherein the given temperature is between 0° C. and 25° C., inclusive.

49. The method of claim 43, wherein the given temperature is between 3° C. and 10° C., inclusive.

50. The method of claim 43, wherein the sample solution has a volume of 1 µL to 100 µL.

51. The method of claim 43, wherein the sample solution has a volume of 5 µL to 30 µL.

52. The method of claim 43, wherein the protein in the protein solution of interest is an antibody.

53. A method of selecting a protein that possesses desired viscosity characteristics, the method comprising:
   (A) providing a solution comprising a given protein;
   (B) carrying out the method of claim 43, wherein the solution of (A) is the protein solution of interest, thereby predicting the viscosity of the protein solution of interest at the given temperature;
   (C) determining that the predicted viscosity of the protein solution of interest at the given temperature is a desired viscosity; and
   (D) selecting the given protein as possessing the desired viscosity characteristics.

54. A method of producing a protein that possesses desired viscosity characteristics, the method comprising:
   (A) selecting an original protein;
   (B) producing a second protein that is a mutated version of the original protein;
   (C) preparing a solution comprising the second protein;
   (D) carrying out the method of claim 43, using the solution of (C) as the protein solution of interest, thereby predicting the viscosity of the protein solution of interest at the given temperature;
   (E) determining that the predicted viscosity of the protein solution of interest at the given temperature is a desired viscosity, thereby determining that the second protein is a protein that possesses the desired viscosity characteristics.

55. The method of claim 54, wherein the desired viscosity is 2000 mPa·s or less.

56. The method of claim 54, wherein the desired viscosity is between 0.1 mPa·s and 1000 mPa·s, inclusive.

57. The method of claim 54, wherein the desired viscosity is between 0.1 mPa·s and 700 mPa·s, inclusive.

58. The method of claim 54, wherein the viscosity of the protein solution of interest is lower than the viscosity of a reference protein solution, wherein the reference protein solution is identical to the protein solution of interest except that the reference protein solution comprises the original protein instead of the second protein.

59. The method of claim 54, wherein the original protein comprises a first amino acid sequence and the second protein comprises a second amino acid sequence, and the first and second amino acid sequences are identical except that the second amino acid sequence comprises His at one or more positions that are not His in the first amino acid sequence.

60. The method of claim 54, wherein the original protein is an antibody.

61. The method of claim 60, wherein the original protein comprises a first antibody heavy chain amino acid sequence and the second protein comprises a second antibody heavy chain amino acid sequence, and the second antibody heavy chain amino acid sequence has an amino acid residue other than His at Kabat numbering position 97.

62. The method of claim 60, wherein the original protein comprises a first antibody heavy chain amino acid sequence and the second protein comprises a second antibody heavy chain amino acid sequence, and the first and second antibody heavy chain amino acid sequences have an identical amino acid residue at Kabat numbering position 97.

63. The method of claim 60, wherein the second protein is an ion concentration-dependent antigen binding antibody.

64. A method of predicting viscosity, at a first temperature, of a protein solution of interest having a first concentration of a protein, the method comprising:
   (a) irradiating, at a second temperature, a sample solution having a second concentration of the protein with X-ray to obtain a scattering pattern, wherein the sample solution and the protein solution of interest are identical except for protein concentration and temperature;

(b) determining, from the scattering pattern, a value for a parameter selected from: apparent maximum particle diameter ($D_{max}^{app}$) of the protein in the sample solution, apparent particle radius of gyration ($R_g^{app}$) of the protein in the sample solution, and apparent molecular weight of the protein in the sample solution; and (c) using the value for the selected parameter to determine, from a predetermined calibration curve, viscosity of the protein solution of interest at the first temperature, wherein the predetermined calibration curve correlates, for each of a plurality of test solution/corresponding solution pairs:

(i) a value for the selected parameter, measured at the second temperature, for the test solution, to (ii) viscosity, measured at the first temperature, of the corresponding solution, wherein each test solution comprises a test protein that can be the same or vary among the plurality of test solutions, wherein each test solution and its paired corresponding solution comprise the same test protein and are identical except for temperature and concentration of the test protein, wherein the concentration of test protein in all of the test solutions is the second concentration and the concentration of test protein in all of the corresponding solutions is the first concentration, and wherein the second concentration is between 1 mg/mL and 100 mg/mL, inclusive.

65. The method of claim 64, wherein the second concentration is between 10 mg/mL and 100 mg/mL, inclusive.

66. The method of claim 64, wherein the second concentration is between 10 mg/mL and 30 mg/mL, inclusive.

67. The method of claim 64, wherein the second concentration is between 15 mg/mL and 30 mg/mL, inclusive.

68. The method of claim 64, wherein the second temperature is between 0° C. and 40° C., inclusive.

69. The method of claim 64, wherein the second temperature is between 0° C. and 25° C., inclusive.

70. The method of claim 64, wherein the second temperature is between 3° C. and 10° C., inclusive.

71. The method of claim 64, wherein the sample solution has a volume of 1 μL to 100 μL.

72. The method of claim 64, wherein the sample solution has a volume of 5 μL to 30 μL.

73. The method of claim 64, wherein the protein in the protein solution of interest is an antibody.

74. A method of selecting a protein that possesses desired viscosity characteristics, the method comprising:

(A) providing a solution comprising a given protein;

(B) carrying out the method of claim 64, wherein the solution of (A) is the protein solution of interest, thereby predicting the viscosity of the protein solution of interest at the first temperature;

(C) determining that the predicted viscosity of the protein solution of interest at the first temperature is a desired viscosity; and (D) selecting the given protein as possessing the desired viscosity characteristics.

75. A method of producing a protein that possesses desired viscosity characteristics, the method comprising:

(A) selecting an original protein;

(B) producing a second protein that is a mutated version of the original protein;

(C) preparing a solution comprising the second protein;

(D) carrying out the method of claim 64, using the solution of (C) as the protein solution of interest, thereby predicting the viscosity of the protein solution of interest at the first temperature;

(E) determining that the predicted viscosity of the protein solution of interest at the first temperature is a desired viscosity, thereby determining that the second protein is a protein that possesses the desired viscosity characteristics.

76. The method of claim 75, wherein the desired viscosity is 2000 mPa·s or less.

77. The method of claim 75, wherein the desired viscosity is between 0.1 mPa·s and 1000 mPa·s, inclusive.

78. The method of claim 75, wherein the desired viscosity is between 0.1 mPa·s and 700 mPa·s, inclusive.

79. The method of claim 75, wherein the viscosity of the protein solution of interest is lower than the viscosity of a reference protein solution, wherein the reference protein solution is identical to the protein solution of interest except that the reference protein solution comprises the original protein instead of the second protein.

80. The method of claim 75, wherein the original protein comprises a first amino acid sequence and the second protein comprises a second amino acid sequence, and the first and second amino acid sequences are identical except that the second amino acid sequence comprises His at one or more positions that are not His in the first amino acid sequence.

81. The method of claim 75, wherein the original protein is an antibody.

82. The method of claim 81, wherein the original protein comprises a first antibody heavy chain amino acid sequence and the second protein comprises a second antibody heavy chain amino acid sequence, and the second antibody heavy chain amino acid sequence has an amino acid residue other than His at Kabat numbering position 97.

83. The method of claim 81, wherein the original protein comprises a first antibody heavy chain amino acid sequence and the second protein comprises a second antibody heavy chain amino acid sequence, and the first and second antibody heavy chain amino acid sequences have an identical amino acid residue at Kabat numbering position 97.

84. The method of claim 81, wherein the second protein is an ion concentration-dependent antigen binding antibody.

* * * * *